(12) United States Patent
Ohara et al.

(10) Patent No.: US 8,009,892 B2
(45) Date of Patent: Aug. 30, 2011

(54) X-RAY IMAGE PROCESSING SYSTEM

(75) Inventors: Hiromu Ohara, Tokyo (JP); Tatsuya Takagi, Tachikawa (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 1047 days.

(21) Appl. No.: 11/840,780

(22) Filed: Aug. 17, 2007

(65) Prior Publication Data

US 2008/0260232 A1    Oct. 23, 2008

(30) Foreign Application Priority Data

Aug. 22, 2006 (JP) ................. 2006-225668

(51) Int. Cl.
*G06K 9/00* (2006.01)
(52) U.S. Cl. .................. 382/132; 382/131; 382/173
(58) Field of Classification Search .......... 382/131, 382/260, 132; 378/62, 37, 121, 207
See application file for complete search history.

(56) References Cited

U.S. PATENT DOCUMENTS

| | | | | |
|---|---|---|---|---|
| 5,644,662 | A * | 7/1997 | Vuylsteke | 382/302 |
| 6,173,084 | B1 * | 1/2001 | Aach et al. | 382/260 |
| 6,212,254 | B1 * | 4/2001 | Wilkins | 378/62 |
| 6,754,398 | B1 * | 6/2004 | Yamada | 382/260 |
| 7,184,516 | B2 * | 2/2007 | Ohara et al. | 378/62 |
| 7,190,761 | B1 * | 3/2007 | Honda et al. | 378/62 |
| 7,356,119 | B2 * | 4/2008 | Anno | 378/62 |
| 2007/0086671 | A1 * | 4/2007 | Kaji | 382/260 |

FOREIGN PATENT DOCUMENTS

| | | |
|---|---|---|
| EP | 0 574 969 A2 | 12/1993 |
| EP | 1 059 811 A2 | 12/2000 |
| EP | 1 069 429 A2 | 12/2000 |
| EP | 1 217 826 A2 | 6/2002 |
| JP | 2001-91479 | 4/2001 |
| JP | 2002-125153 | 4/2002 |
| WO | WO 98/55916 | 12/1998 |

OTHER PUBLICATIONS

Chinese Office Action from Application No. 200710141672.4 dated May 12, 2010.
European Search Report dated Nov. 26, 2007.

* cited by examiner

*Primary Examiner* — Daniel G Mariam
*Assistant Examiner* — Nancy Bitar
(74) *Attorney, Agent, or Firm* — Finnegan, Henderson, Farabow, Garrett & Dunner, L.L.P.

(57) ABSTRACT

An X-ray image processing system, comprises: a radiographing section including an X-ray source to emit X-rays for an object to be radiographed and an image detector to detect X-rays having passed through the object, wherein the radiographing section is adapted to conduct a phase contrast radiography by providing a space between the object and the image detector and by irradiating X-rays having an X-ray energy of 15 to 30 (keV) from the X-ray source to the object; an image data producing section to produce X-ray image data of X-ray image detected by the image detector; an image processing section to applying an image processing including a noise reducing process for the produced X-ray image data; and an output section to output the processed image data applied with the image processing.

24 Claims, 16 Drawing Sheets

DIFFERENTIAL IMAGE SIGNAL (1D)

EDGE COMPONENT SORTATION (1D)

2-DIMENSIONAL FILTER COEFFICIENT

| 0.012 | 0.026 | 0.033 | 0.026 | 0.012 |
|-------|-------|-------|-------|-------|
| 0.026 | 0.055 | 0.071 | 0.055 | 0.026 |
| 0.033 | 0.071 | 0.092 | 0.071 | 0.033 |
| 0.026 | 0.055 | 0.071 | 0.055 | 0.026 |
| 0.012 | 0.026 | 0.033 | 0.026 | 0.012 |

1-DIMENSIONAL FILTER COEFFICIENT

| 0.11 |
|------|
| 0.23 |
| 0.30 |
| 0.23 |
| 0.11 |

X-RAY IMAGE PROCESSING SYSTEM

CROSS-REFERENCE TO RELATED APPLICATION

This application is based on Japanese Patent Application No. 2006-225668 filed on Aug. 22, 2006, in Japanese Patent Office, the entire content of which is hereby incorporated by reference.

BACKGROUND OF THE INVENTION

The present invention relates to an X-ray image processing system by which X-ray image data is generated by the X-ray photography and outputted.

A baby, an infant, or a child of six years old or under (hereinafter, called a child) is different from an adult, because almost marrow are red marrow, the effect due to the exposure to radiation is large. Accordingly, the reduction of exposure amount is more required than adult and when the X-ray photographing is conducted on child, because the exposure amount is suppressed to the minimum, it is necessary that the photographing condition is adjusted and the reduction of X-ray radiation amount is intended.

The X-ray image obtained by the photography by a small amount of radiation is, because the signal value is totally lowered, noise is increased. Conventionally, on the obtained X-ray image, it is responded by conducting the noise removal processing. or noise reduction processing (for example, refer to Tokkai No. 2002-125153).

However, when the noise reduction processing is conducted on the X-ray image photographed by the small amount of radiation, the effect of some degree is obtained and easy looking image quality is obtained, however, the sharpness is lowered due to the influence of the noise removal, (because the original signal part is attenuated by the noise removal). Accordingly, the border part of the region becomes un-sharp, and the utility for the diagnosis is lowered. In order to avoid such a problem, the X-ray amount at the photographing can not be decreased enough, as a result, it is a difficult condition to intend the enough reduction of exposure amount.

SUMMARY

The object of the present invention is to provide an X-ray image processing system by which the high quality X-ray image can be outputted even when it is a photography with a small amount of radiation.

The above object can be attained by systems or methods described in the following items.

Item 1. An X-ray image processing system, comprises:

a radiographing section including an X-ray source to emit X-rays for an object to be radiographed and an image detector to detect X-rays having passed through the object, wherein the radiographing section is adapted to conduct a phase contrast radiography by providing a space between the object and the image detector and by irradiating X-rays having an X-ray energy of 15 to 30 (keV) from the X-ray source to the object;

an image data producing section to produce X-ray image data of X-ray image detected by the image detector;

an image processing section to applying an image processing including a noise reducing process for the produced X-ray image data; and an output section to output the processed image data applied with the image processing.

Item 2. In the X-ray image processing system described in Item 1, when D represents a focal size of the X-ray source, R1 represents a distance between the X-ray source and the object and R2 represents a distance between the object and the X-ray detector, the X-ray source, the object and the X-ray detector are arranged to satisfy the following formulas:

$(D-7)/200 \leq R1 \leq 1.0$ (m), and $0.15 \leq R2 \leq 1.0$ (m)

Item 3. In the X-ray image processing system described in Item 2, R1 satisfies the following formula:

$0.3 \leq R1 \leq 1.0$ (m)

Item 4. In the X-ray image processing system described in Item 2, R2 satisfies the following formula:

$0.3 \leq R2 \leq 1.0$ (m)

Item 5. In the X-ray image processing system described in Item 2, the X-ray source has a focal size D of 30 to 200 μm.

Item 6. In the X-ray image processing system described in Item 5, the X-ray source has a focal size D of 50 to 120 μm.

Item 7. In the X-ray image processing system described in Item 2, when M represents an enlargement ratio represented by Formula of $((R1+R2)/R1)$ in the phase contrast radiography, M satisfies the following formula:

$1.2 \leq M \leq 5$

Item 8. In the X-ray image processing system described in Item 7, M satisfies the following formula:

$1.5 \leq M \leq 3$

Item 9. In the X-ray image processing system described in Item 1, the image processing includes a gradation converting process, and after the image processing section applies the gradation converting process for the X-ray image data in the image processing, the image processing section applies the noise reducing process for the X-ray image data so as to form the processed image data.

Item 10. In the X-ray image processing system described in Item 1, the image processing includes a gradation reversing process, and after the image processing section applies the noise reducing process for the X-ray image data in the image processing, the image processing section applies the gradation reversing process for the X-ray image data so as to form the processed image data.

Item 11. In the X-ray image processing system described in Item 1, the image processing section comprises:

a decomposition processing section to conduct a multiple-resolution conversion for X-ray image data inputted from the image data producing section so as to obtain unsharp image data for each of plural different frequency bands;

a conversion processing section to conduct a converting process for at least one of the inputted X-ray image data and the unsharp image data of the plural different frequency bands so as to obtain converted image data and to obtain difference image data by subtracting between the converted image data and image data in a frequency band neighboring the converted image data or image data in the highest frequency band; and a reconstruction processing section to add the difference image data to the inputted X-ray image data so as to obtain the processed image data.

Item 12. In the X-ray image processing system described in Item 11, the conversion processing section comprises:

an information acquiring subsection to acquire at lest one of edge information and noise information in the inputted X-ray image data;

a smoothing correcting section to conduct at lest one of an edge smoothing process and a noise smoothing process for at least one of the inputted X-ray image data and the unsharp image data of the plural frequency bands based on at least one of the edge information and the noise information and thereafter conduct a density-related correcting process for the smoothed image data so as to obtain the converted image data.

Item 13. In the X-ray image processing system described in Item 12, the smoothing correcting section comprises:

an edge component adjusting subsection including:
a first converting section to obtain first converted image data by conducting the noise smoothing process for at least one of the inputted X-ray image data and the unsharp image data of the plural frequency bands based on at least one of the edge information and the noise information and thereafter to conduct the density-related correcting process for the noise-smoothed image data so as to obtain the first converted image data, and
a first difference adjusting section to obtain difference image data mainly composed of edge components by subtracting the first converted image data and image data in a frequency band neighboring the first converted image data or image data in the highest frequency band and to multiply the difference image data with a predetermined edge adjustment coefficient so as to obtain edge component-adjusted difference image data; and
a noise component adjusting section including:
a second converting section to obtain second converted image data by conducting the edge smoothing process for at least one of the inputted X-ray image data and the unsharp image data of the plural frequency bands based on at least one of the edge information and the noise information and thereafter to conduct the density-related correcting process for the edge-smoothed image data so as to obtain the second converted image data, and
a second difference adjusting section to obtain difference image data mainly composed of noise components by subtracting the second converted image data and image data in a frequency band neighboring the second converted image data or image data in the highest frequency band and to multiply the difference image data with a predetermined noise adjustment coefficient so as to obtain noise component-adjusted difference image data.

Item 14. In the X-ray image processing system described in Item 12, the edge information includes information representing at least one of pixel positions of edge components, signs of image data, directions of edge components, and pixel positions of inflection points, and the noise information includes information represent at least one of local dispersion values, entropy values and pixel positions of noise components.

Item 15. In the X-ray image processing system described in Item 12, the noise smoothing process conducts smoothing two dimensionally for pixels being not edge components and conducts smoothing one dimensionally for pixels being edge components in a direction other than an edge inclination direction or a direction perpendicular to an edge inclination direction.

Item 16. In the X-ray image processing system described in Item 12, the edge smoothing process conducts smoothing one dimensionally for pixels being edge components only in an edge inclination direction.

Item 17. An X-ray image processing method of processing an X-ray image of a child of six years old or under, comprises the steps of:

arranging the child and a detector to provide a space therebetween;
irradiating X-rays having an X-ray energy of 15 to 30 (keV) from the X-ray source to the child with a phase contrast radiography;
producing X-ray image data of the child by detecting x-rays having passed through the child;
applying a noise reducing process for the X-ray image data on an image processing condition for children.

Item 18. In the X-ray image processing method described in Item 17, when D represents a focal size of the X-ray source, R1 represents a distance between the X-ray source and the child and R2 represents a distance between the child and the X-ray detector, the X-ray source, the child and the X-ray detector are arranged to satisfy the following formulas:

$$(D-7)/200 \leq R1 \leq 1.0 \text{ (m), and } 0.15 \leq R2 \leq 1.0 \text{ (m)}$$

Item 19. In the X-ray image processing method described in Item 18, R1 satisfies the following formula:

$$0.3 \leq R1 \leq 1.0 \text{ (m)}$$

Item 20. In the X-ray image processing method described in Item 18, R2 satisfies the following formula:

$$0.3 \leq R2 \leq 1.0 \text{ (m)}$$

Item 21. In the X-ray image processing method described in Item 18, the X-ray source has a focal size D of 30 to 200 μm.

Item 22. In the X-ray image processing method described in Item 21, the X-ray source has a focal size D of 50 to 120 μm.

Item 23. In the X-ray image processing method described in Item 18, when M represents an enlargement ratio represented by Formula of $((R1+R2)/R1)$ in the phase contrast radiography, M satisfies the following formula:

$$1.2 \leq M \leq 5$$

Item 24. In the X-ray image processing method described in Item 23, M satisfies the following formula:

$$1.5 \leq M \leq 3$$

According to the invention, the X-ray image is obtained by the phase contrast photographing and the noise reduction processing is conducted on it. Because in the X-ray image obtained by the phase contrast photographing, the side edge of the subject organization is edge emphasized, in the noise reduction processing, the edge component is easily extracted by separating from the noise component, and the edge emphasis and the noise suppression can be accurately conducted. That is, because the brilliant and high quality processed image can be obtained, in the photography for child, even when the X-ray amount for the photography is a small amount of radiation, the X-ray image with image quality enough for trace-reading can be obtained. Therefore, when child is a photographing subject, the exposed amount can be suppressed to the minimum. Further, because the original image itself becomes sharp by the phase contrast effect, even when it is slightly blurred to the original image, the image after the noise reduction still has the high sharpness.

According to the invention, when the gradation conversion processing and the noise reduction processing are combined, not only conducting the edge emphasis and the noise suppression, the contrast or the density range can also be adjusted.

According to the invention, when the gradation reversal processing and the noise reduction processing are combined, not only conducting the edge emphasis, noise suppression, by the gradation reversing, the visibility of the structure in the image can be increased.

BRIEF DESCRIPTION OF THE DRAWINGS

FIG. 11($b$) is a view showing the classification of the edge component, non-edge component for the image signal of (a).

FIG. 12($b$) is a view showing an example of 1-dimensional smoothing filter coefficients.

FIG. 15($b$) is a view showing the response to the density of the correction function corresponding to the edge smoothing processing.

DETAILED DESCRIPTION OF THE PREFERRED EMBODIMENT

In the present embodiment, when the X-ray image whose sharpness of side edge part is high is obtained by the phase contrast radiography, and conducting the noise reduction processing on the X-ray image, an example of the X-ray image processing system by which even under a small amount of radiation (the low dose), the high image quality X-ray image can be provided, will be described.

Initially, a structure will be described.

Figure 1:
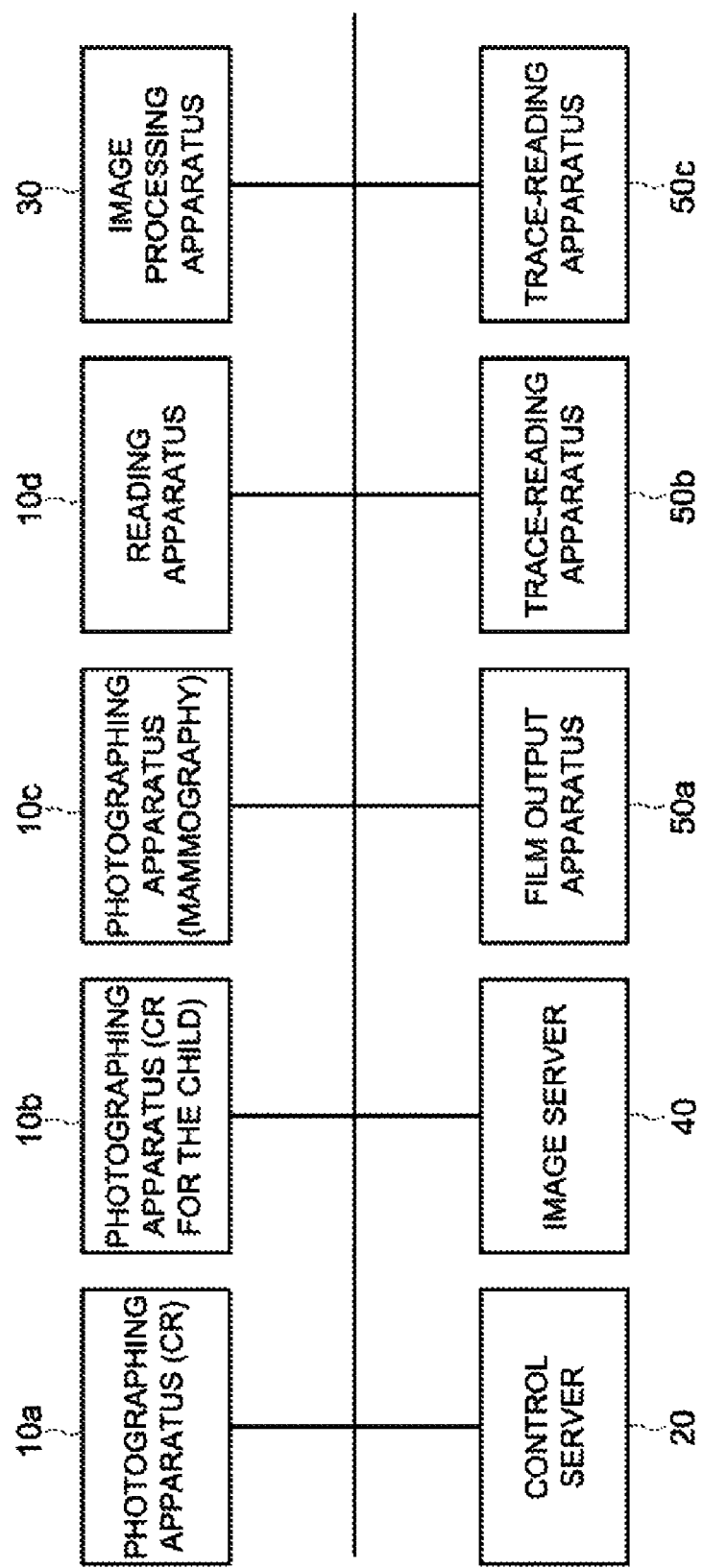
FIG. 1 is a view showing the system structure of X-ray image processing system in the present embodiment.

In FIG. 1, the system structure of the X-ray image processing system 1 in the present embodiment is shown. As shown in FIG. 1, the X-ray image processing system is structured by providing with photographing apparatus 10$a$-10$c$, reading apparatus 10$d$, control server 20, image processing apparatus 30, image server 40, film output apparatus 50$a$, image diagnostic apparatus (trace-reading apparatus) 50$b$, 50$c$. Each apparatus is structured in the manner that they can mutually communicate through a network N.

The X-ray image processing system is a system by which each kind of image processing is conducted by the image processing apparatus 30 on the X-ray image data generated in the photographing apparatus 10$a$, 10$c$, or the reading apparatus 10$d$, by the X-ray photographing and the processed image is generated, and it is outputted from the film output apparatus 50$a$ or the image diagnostic apparatus 50$b$, 50$c$. Hereupon, FIG. 1 is an example of the system structure and it is not limited to this.

Change of the number of apparatus, addition of other apparatus may be appropriately structured.

The photographing apparatus 10$a$-10$c$ is the apparatus by which the X-ray photographing and/or the data generation of X-ray image is conducted. The photographing apparatus 10$a$ is a CR (Computed Radiography) apparatus for the general photographing, the photographing apparatus 10$b$ is a CR apparatus for child photographing, the photographing apparatus 10$c$ is a CR apparatus for the mammography. In the photographing apparatus 10$a$-10$c$, there is an apparatus of a type which conducts the X-ray photographing and the X-ray image generation, and a type which only conducts the X-ray photographing by using a portable image detector. The reading apparatus 10$d$ is an apparatus by which the X-ray image is read from the image detector used in the photographing in the photographing apparatus 10$a$-10$c$ of the latter type and the data is generated.

The control server 20 is a control apparatus by which a sequence of processing from the photographing by the photographing apparatus 10$a$-10$c$ to the generation, storing, output in the X-ray image processing system 1 are totally controlled. As the control server 20, a general computer apparatus can be applied, and by using the program for the control, the control operation is conducted.

The control server conducts the control by using the photographic order information. The photographic order information is the photographing indication information by which the doctor specified condition about the photographing content or the generation condition of the image is shown, and is generated in HIS (Hospital Information System) or RIS (Radiology Information System) which are not shown, and sent to the control server 20. In the control server 20, this photographing order information is analyzed and distributed to the photographing apparatus corresponding to the photographing content in the photographing apparatus 10$a$-10$c$.

The control server 20 conducts the transfer control to the image processing apparatus 30 of the X-ray image generated in the photographing apparatus 10$a$-10$c$, or the reading apparatus 10$d$. In this case, when the child photographing is specified by the photographing order information, the control information by which it is indicated that the image processing is conducted by the image processing condition for the child, is generated and transmitted to the image processing apparatus 30 together with the X-ray image.

The image processing apparatus is an apparatus which conducts each kind of image processing on the X-ray image and generates its processed image.

The image server 40 is a server which stores the X-ray image data in the large capacity memory and controls. The image server 40 transmits the X-ray image data to the film output apparatus 50$a$, image diagnostic apparatus 50$b$ following the indication of the control server 20.

The film output apparatus 50$a$ is an apparatus which forms the X-ray image on the film, and outputs it. Image diagnostic apparatus 50$b$, 50$c$ are terminal apparatus used for the observation of the X-ray image of the doctor and the X-ray image is displayed and outputted on the monitor.

Next, the photographing apparatus 10$b$, the image processing apparatus 30 according to the present invention 30 will be detailed. The photographing apparatus 10$b$ is an apparatus by which the phase contrast photographing is conducted by making the child the subject W. The photographing apparatus 10$b$ is structured by providing with the photographing part 3 and the main body part 4 which conducts the photographing control.

The photographing part 3 is formed arm-like, and structured in the manner that it can be up and down by making the main body part 4 the column. In the arm part of the photographing part 3, the X-ray source 2 and a holding part 5 are arranged in opposition. The holding part 5 holds the image detector 6 and fixes the position. The holding part 5 is structured in the manner that it can be up and down along the column part of the photographing part 3. When these photographing part 3 and the holding part 5 are risen and fallen, and their height positions are changed, the photographing distance can be adjusted.

The main body part 4 is structured by providing with the computer structured by the CPU (Central Processing Unit) or RAM (Random Access Memory), ROM (Read Only Memory), operation part. The main body part 4 controls the rise and fall of the photographing part 3, the rise and fall of the holding part 5, and controls the irradiation operation of the X-ray by the X-ray source 2.

The X-ray source 2 a source which generates the X-ray and irradiates to the subject. For the X-ray source 2, the X-ray tube having the focal size D (μm) adequate for the phase contrast photographing whose photographing subject is the child, is used. It is preferable that this focal size D is 30-200 (μm), further, 50-120 (μm).

Figure 2:
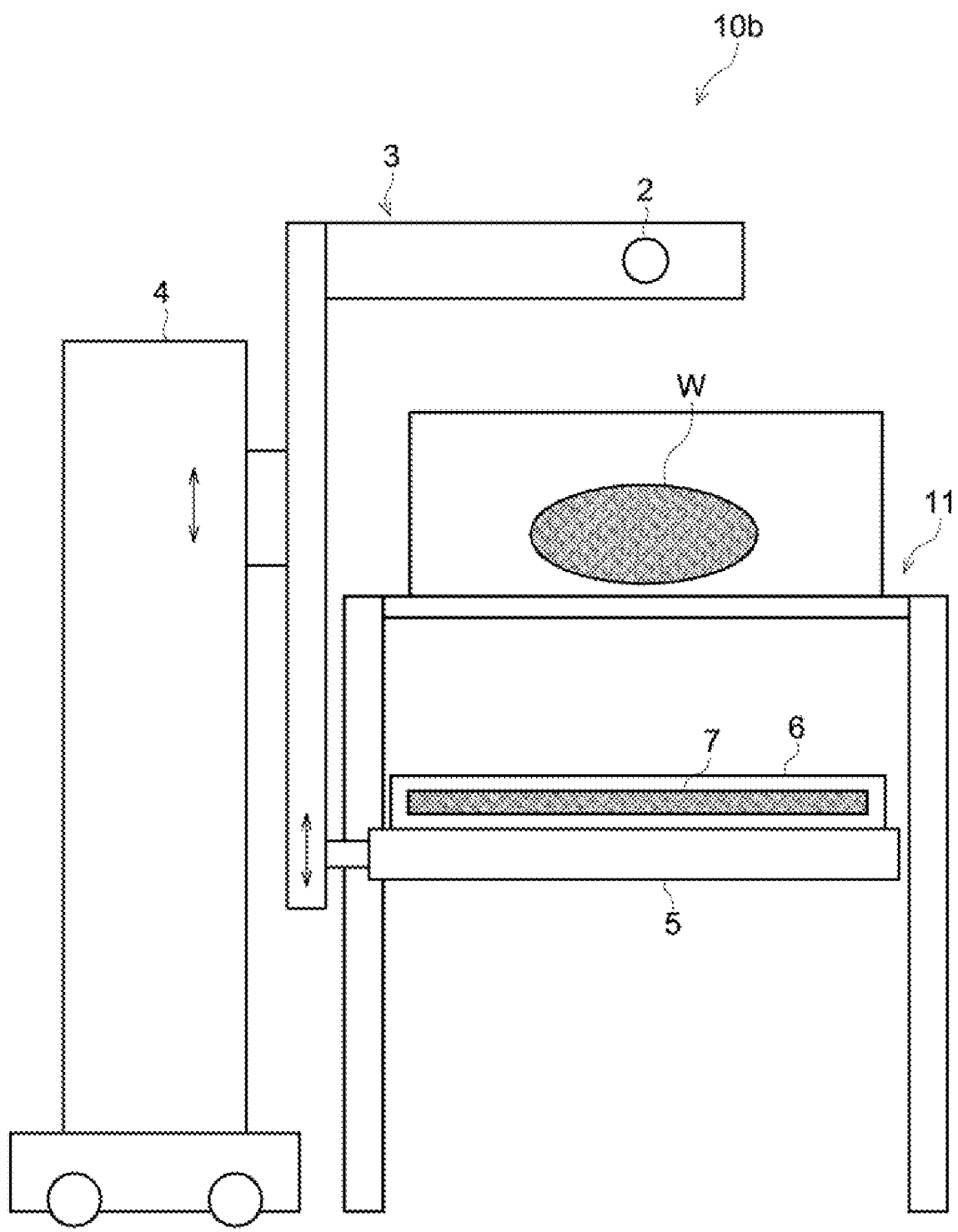
FIG. 2 is a view showing an example of a X-ray photographing apparatus.

The subject W of the photographing object is the child. The photographing is conducted under the condition that the child is accommodated in the infant incubator 11, and the height position of the X-ray source 2 and holder 5 is adjusted correlating to the height position of the child. In the infant incubator 11, as shown in FIG. 2, the case for the child care is provided on the bed-like supporting table.

The image detector 6 is a detector in which the fluorescent body plate 7 is accommodated in the casing called cassette. The fluorescent body plate 7 is the X-ray detector by which the X-ray energy is absorbed and accumulated. The image detector 6 detects the X-ray which is irradiated from the X-ray source 2 and arrived through the subject W, by the fluorescent plate 7. After that, the image detector 6 is loaded in the reading apparatus 10d, and the image visualizing is conducted. The reading apparatus 10d irradiates the excitation light such as the laser light and when the stimulation light projected from the fluorescent body plate 7 is photoelectric converted into the image signal, the image signal is generated.

Hereupon, an example of the image detector 6 in which the fluorescent body plate 7 is accommodated in the cassette will be described, however, as the image detector 6, somewhat else, FPD (Flat Panel Detector) can also be applied. FPD is a plate in which the conversion elements for generating the electric signal corresponding to the incident X-ray amount, are arranged matrix-like, and a point that in FPD, the electric signal is directly generated, is different from the fluorescent body plate 7. When FPD is applied, the electric signal generated in the FPD is A/D converted, and obtained digital image data is outputted to the main body part 4.

Figure 3:
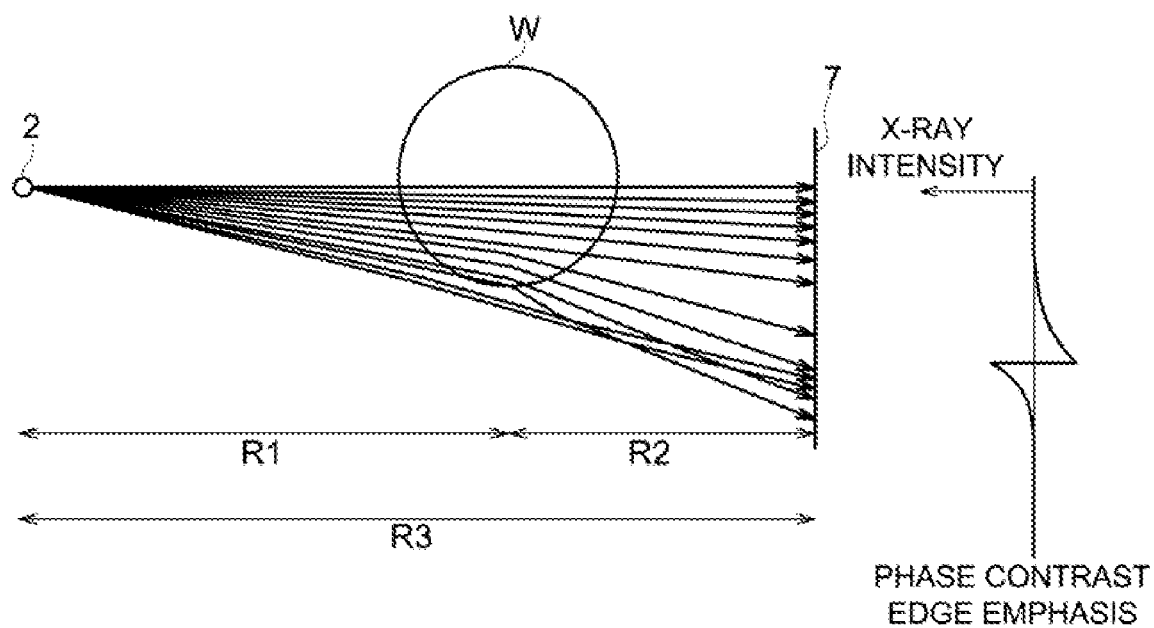
FIG. 3 is a view explaining the phase contrast photographing and the phase contrast effect.

Next, the phase contrast photographing conducted by the photographing part 3, will be described below. The phase contrast photographing is the photographic which is different from the ordinary enlarge photographing, the photographic condition such as the photographing distance or the irradiation condition of the X-ray is adjusted so that the edge emphasis effect can be obtained. FIG. 3 is a view explaining the outline of the phase contrast photographing. In the case of general photographing, the image detector 6 is arranged adjoining to the subject W so that the X-ray transmitted the subject W can be received soon by the image detector 6. Accordingly, the X-ray image obtained by the general photographing is almost same size as the life size (which is called that it is the same size as the subject W).

On the one hand, in the phase contrast photographing as shown in FIG. 3, the distance is provided between the subject W and the image detector 6. That is, the subject W and the image detector 6 are separated. In this case, after the X-ray irradiated cone beam-like from the X-ray source 2 transmits the subject W, because it arrives at the image detector 6 still cone beam-like, the obtained X-ray image is the enlarged size compared to the life size.

The magnifying power M at this time, when the distance from the X-ray source 2 to the subject W is R1, the distance from the subject W to the image detector 6 is R2, the distance from the X-ray source 2 to the image detector 6 is R3 (R3=R1+R2), can be found by the following equation (1).

$$M=R3/R1 \tag{1}$$

The magnifying power M is can be adjusted by changing the ratio of the distance R1, R2.

In the photographing apparatus 10b, as disclosed in Tokkai No. 2001-91479, when the setting of R1, R2, R3 and the focal size D is a predetermined range, the phase contrast photographing by which the edge emphasis effect of the subject W side edge can be obtained is conducted.

The photographic condition written in Tokkai No. 2001-91479 is that the focal size D of the X-ray source 2 is D≧30, the distance R1 is R1≧(D−7)/200, preferably, 0.3-1.0 (m), the distance R2 is R2≧0.15, preferably, 0.3-1.0 (m). By this condition, in the X-ray image obtained by the photographing, the edge emphasis effect can be obtained. Further, when the total length in the photographing room is considered, the photographing within this range is preferable.

The edge emphasis effect will be described.

In the X-ray image obtained by the phase contrast photographing, as shown in FIG. 3, the phenomenon that the X-ray refracted by passing the side edge of the subject W is overlapped with the X-ray transmitted without through the subject W, the X-ray intensity of the overlapped part becomes strong, is generated. Therefore, the phenomenon that, in the part of the side edge inside, the X-ray intensity becomes weak, is generated. Hereby, the edge emphasis action (which is called edge effect, or also called the phase contrast effect) is performed, and the X-ray image in which the side edge part is sharply drawn and the visibility is high is obtained.

Figure 4:
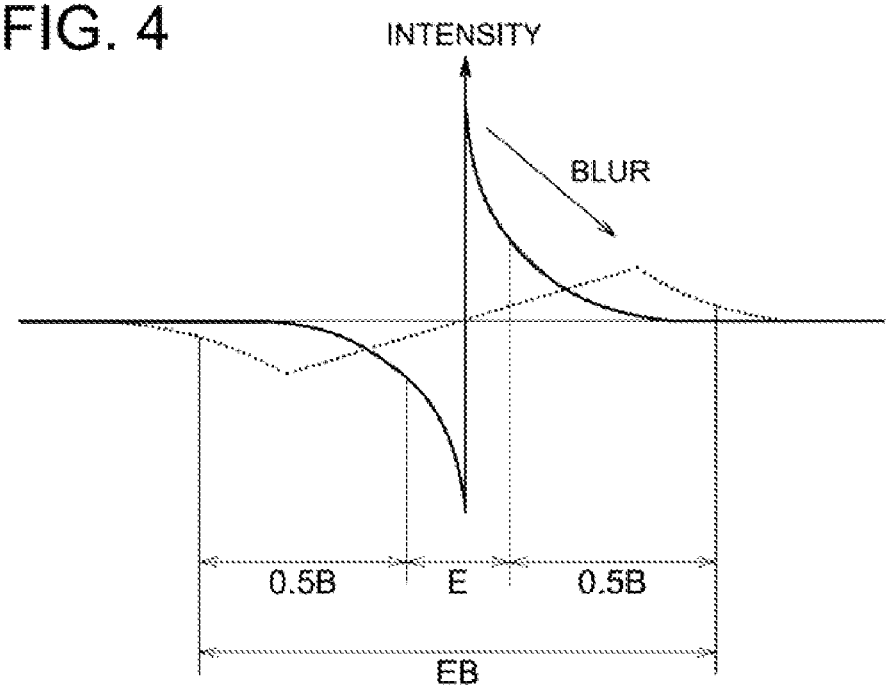
FIG. 4 is a view showing the relationship between the edge intensity in the phase contrast effect and the blur.
Figure 5:
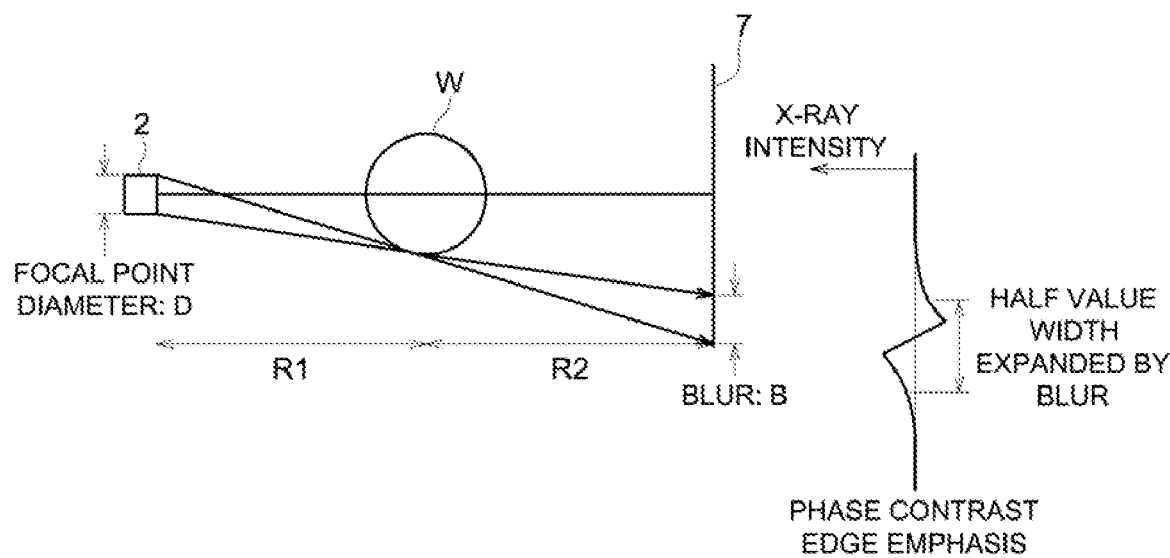
FIG. 5 is a view explaining the case where the blur is generated in the phase contrast effect.

When it is assumed that the X-ray source 2 is a point source, the X-ray intensity in the side edge part is as shown in FIG. 4 by a solid line. E shown in FIG. 4 shows the half value width of the edge emphasis, and can be found by the following equation (2). The half value width E shows the distance between the mount and valley of the edge.
[Arith 1]

$$E = 2.3\left(1 + \frac{R2}{R1}\right)^{1/3} \cdot \{R2 \cdot \delta \cdot (2r)^{1/2}\}^{2/3} \tag{2}$$

Where,
δ: the refractive difference at the part at which the refraction of the X-ray is generated
r: radius of object (subject)

However, in the medical job site or the non-destructive inspection facility, as the X-ray source 2, the Coolidge X-ray tube (called also thermal electronic X-ray tube) is widely used, because in this Coolidge X-ray tube, the focal size is large some degree, it can not be assumed as an ideal point ray source. In this case, a phenomenon of geometrical un-sharpness that the half value width E of the edge emphasis is spread, and the intensity is lowered, is generated and becomes the X-ray intensity as shown by a dotted line in FIG. 4. This geometric un-sharpness is called blur.

In the case where the half value width of the edge emphasis is EB when the blur is generated, EB can be found from the following equation (3).

[Arith 2]

$$EB = 2.3\left(1 + \frac{R2}{R1}\right)^{1/3} \cdot \{R2 \cdot \delta \cdot (2r)^{1/2}\}^{2/3} + D \cdot \frac{R2}{R1} \quad (3)$$

In the equation, the definition of δ and r is the same as the equation (2).

Further, EB adds B showing the largeness of the blur to the edge emphasis half value width E when there is no blur, and shown by EB=E+B. As described above, the smaller the focal size D of the X-ray source is, the blur is decreased, the larger the obtained edge effect is.

When the child is the photographic object, in the photographic apparatus 10b, the photographing is conducted by the photographic condition for the child. The photographic condition for the child is that, when the phase contrast photographing is conducted, the focal size (focal point diameter) D of the X-ray source 2 is 30-200 (μm), preferably, 50-120 (μm), the magnifying power M is 1.2≦M≦5, preferably, 1.5≦M≦3, the distance R1 is R1≧(D−7)/200, preferably, 0.3-1.0 m, the distance R2 is R2≧0.15, preferably, 0.3-1.0 (m). Because for the child, the photographic subject is small, the magnifying power M can be larger than the adult. Further, when the W (tungsten) tube is used for the X-ray source 2, it is preferable that the tube voltage is 20-50 (kVp) which is low voltage, and the irradiated X-ray energy is 15-30 (keV). The cartilage of the child is different from the adult, and has the nature close to the soft tissue (muscle or fat). Accordingly, when the above-described energy range is applied, the increase of the contrast (signal value difference) between the cartilage and the soft tissue surrounding the cartilage can be intended.

Figure 6:
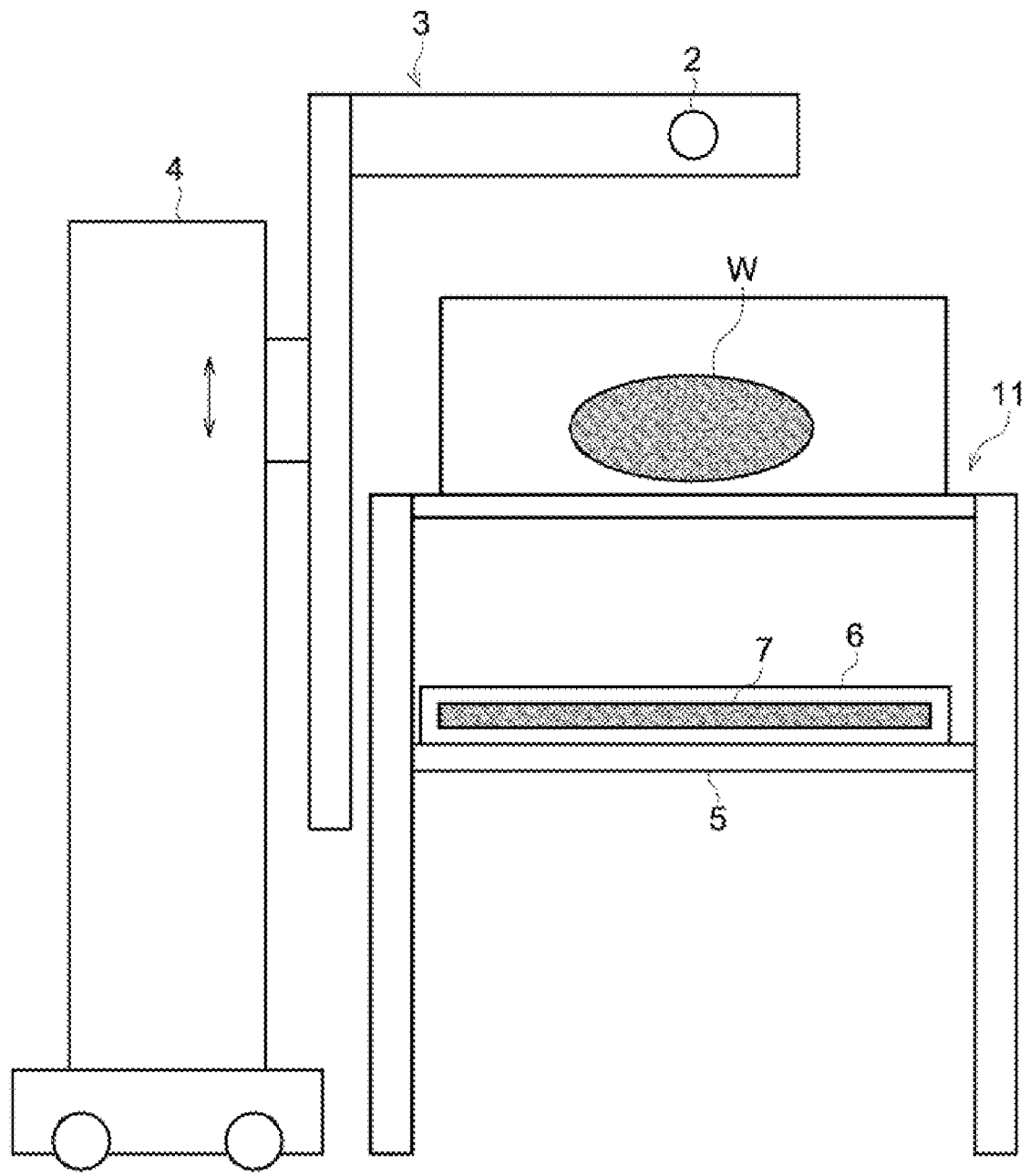
FIG. 6 is a view showing another example of the X-ray photographing apparatus.

Hereupon, as shown in FIG. 6, in the photographing part 3 of the photographing apparatus 10b, it may also be allowed that only the X-ray source 2 is mounted, in the infant incubator 11, the holder for holding the image detector 6 is provided in the lower part of the subject W and the photographing is conducted. In this case, because the distance R2 between the subject W and the image detector 6 is fixed, the magnifying power M is adjusted by the distance R1 between the X-ray source 2 and the subject W. Further, the photographing apparatus 10b may also be ambulatory one.

Next, The image processing apparatus 30 will be described.

Figure 7:
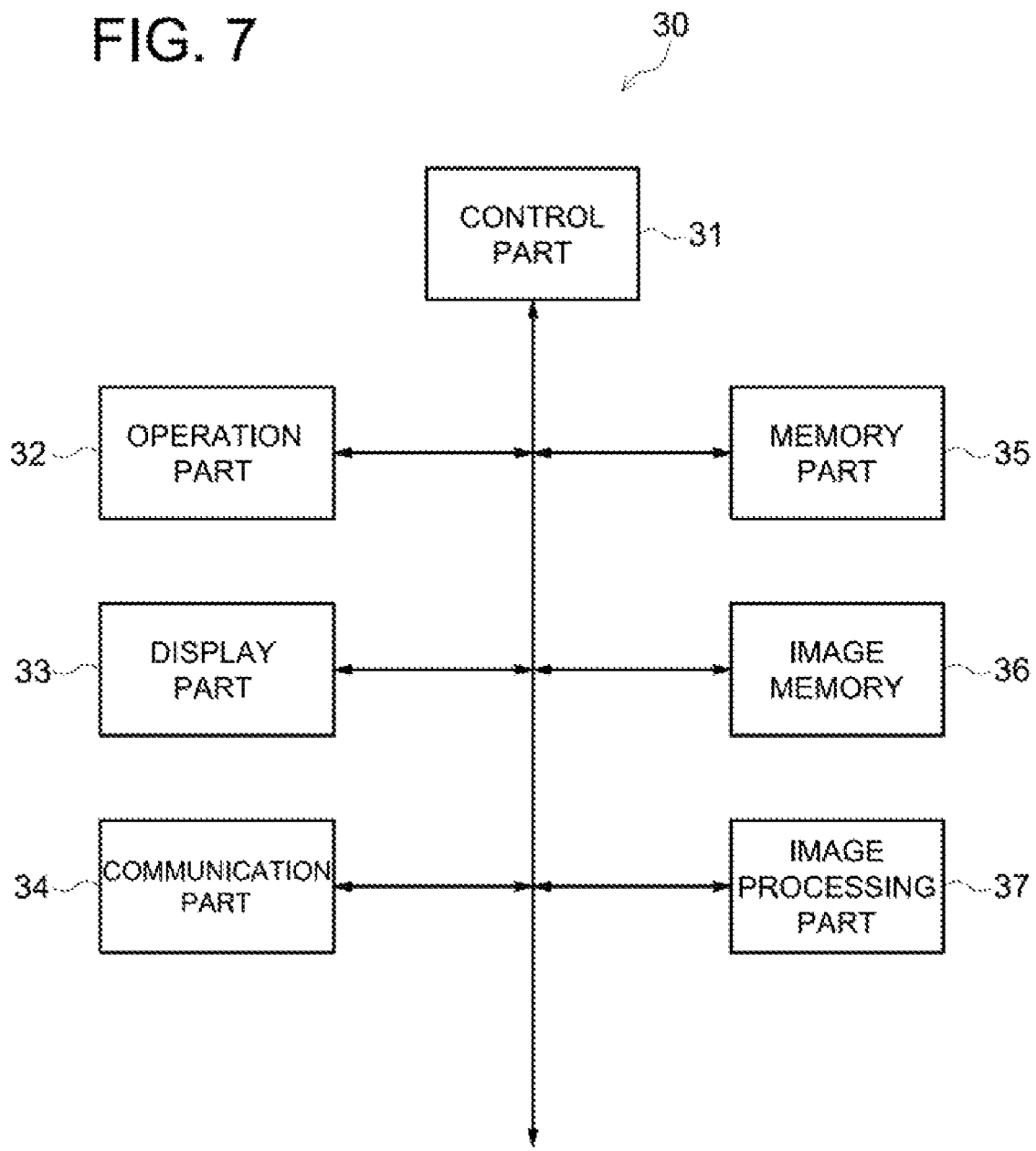
FIG. 7 is a view showing the internal structure of an image processing apparatus.

The image processing apparatus 30 is structured by providing with, as shown in FIG. 7, The control part 31, operation part 32, display part 33, communication part 34, memory part 35, image memory 36, image processing part 37.

The control part 31 is structured by CPU (Central Processing Unit), RAM (Random Access Memory), each kind of control program stored in The memory part 35 is read from CPU, and developed into RAM, and according to these programs, each kind of calculation or central control of each part is conducted.

The operation part 32 has a mouse or key board and The operation signal corresponding to these operations is generated, and outputs to the control section 31.

The display part 33 has a display and according to The control of The control part 31, displays each kind of display image screen.

The communication part 34 has an interface for the communication such as the network interface card, and communicates with the outside apparatus on the network.

The memory part 35 stores each kind of program carried out in the control part 31 or image processing program carried out in the image processing part 37, parameters or data necessary for them.

The image memory 36 is a memory for storing the X-ray image of The image processing object or the processing image after the processing.

The image processing part 37 carries out each kind of image processing according to the image processing program. As the image processing, after, as the before processing, the irradiation field recognition processing, the setting of concerning area are conducted, Each kind of image processing such as the gradation conversion processing, gradation reversal processing, noise reduction processing can be conducted.

In the image processing part 37, the image processing condition corresponding to the purpose of use of photographing which is for the child, or for the general photographing, is previously determined, and the image processing is conducted according to the image processing condition specified by the control part 31.

AS The image processing condition, The kind of conducted image processing, order, processing parameter in each image processing are determined. The image processing condition for the child is that The noise reduction processing is conducted after the image conversion processing. Alternatively, The gradation reversal processing may also be conducted after The noise reduction processing. The processing parameter for the child adopted in each image processing will be described blow together with the description of each image processing.

(Gradation Conversion Processing)

The gradation conversion processing is the processing for adjusting the density at the image output, contrast. When the doctor diagnoses the existence of disease in the human structure by the trace-reading of the X-ray image, he judges the existence of disease based on the density of the structure in the X-ray image, or the contrast (gradation property). Therefore, when it is adjusted to the density appropriate for the trace-reading, contrast, it can support the detecting operation of the disease of the doctor.

The gradation conversion processing is conducted in 2 stages of (1) normalizing processing, (2) conversion processing of by using the basic LUT (Look-UP Table), and the gradation conversion is conducted so that it becomes finally desired signal value range, gradation characteristic. Conventionally, from the back ground that the screen film system is adopted for the photographing, also in the present in which the digital processing system by using the image detector is adopted, in order to maintain the trace-reading capability (diagnostic performance) of the doctor, the conversion processing of the input signal (reading signal) is conducted aiming at the gradation characteristic (contrast) acquired by the screen/film system.

Figure 8:
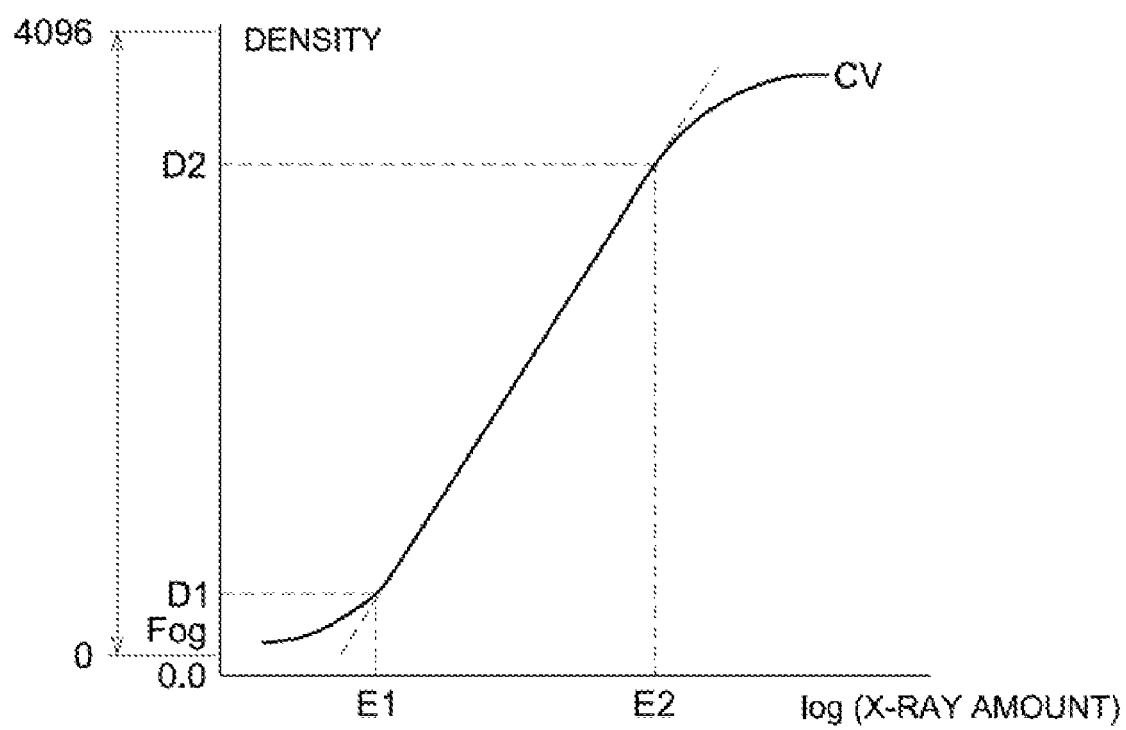
FIG. 8 is a view showing the gradation conversion characteristic which is a target in the gradation conversion processing.

The gradation characteristic obtained in The screen/film system, is The S letter-shaped curve CV as shown in FIG. 8. In The gradation conversion processing, The LUT showing this gradation characteristic is prepared as the basic LUT, after each signal adjustment is conducted for the object image by the normalizing processing, the signal value is converted by using this basic LUT.

Figure 9:
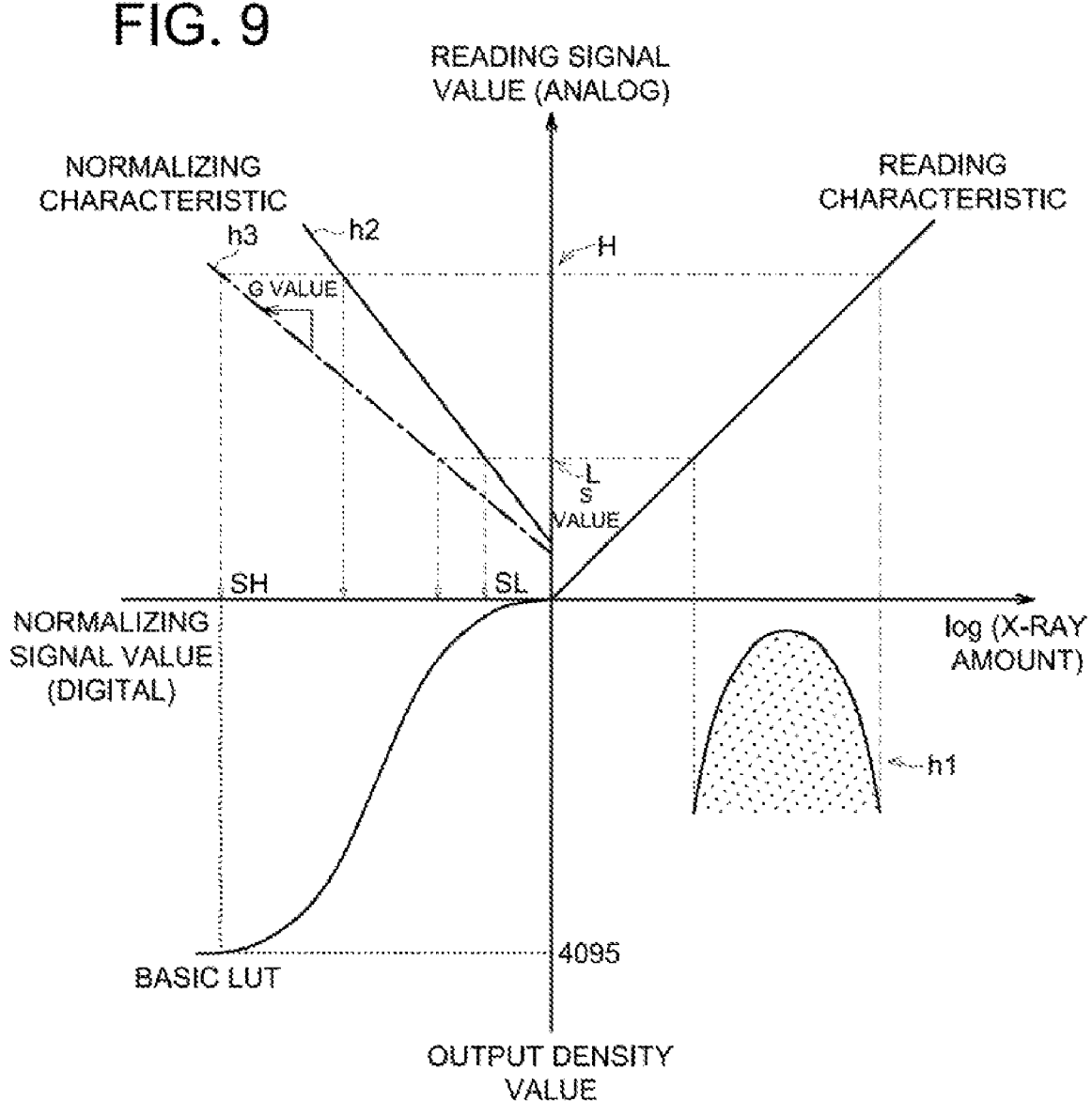
FIG. 9 is a view showing a flow of conversion of the signal value at the time of the gradation conversion processing.

The relationship between the X-ray amount detected by the image detector (in the case of fluorescent plate) and the signal value (X-ray image data) of the X-ray image outputted finally corresponding to that X-ray amount is shown in FIG. 9.

In the coordinate system of FIG. 9, the first quadrant shows the reading characteristic, and shows the relationship between the arrived X-ray amount to the image detector and the read signal value (analog signal value). Further, the second quadrant shows the normalizing characteristic, and shows the relationship between its read signal and the normalized signal value (digital signal value) after the normalizing processing is conducted. The third quadrant shows the gradation conversion characteristic, and shows the relationship between the normalized signal value and the output density value (digital density signal value) converted by the basic LUT. Hereupon, herein, the output density values (output image density levels) correspond to the resolving power of 12 bits of 0-4095.

In The second quadrant, when the straight lone showing the normalizing characteristic changes its inclination, the range of The output value (largeness between SH–SL can be adjusted, and together with it, The contrast of The whole of image can be changed. This inclination is defined as G value. Further, when the bias point of the straight line showing the gradation conversion characteristic is changed, the ups and downs of the whole of range of the output (movement of SH–SL) is adjusted, hereby, the density of the whole image can be changed. This bias point is defined as S value.

For example, when the cases where the normalization is conducted in the straight line h2 shown in FIG. 9, and the straight line h3 are compared, when G value is increased, the normalizing signal value corresponding to the subject W corresponds to the straight line area of the basic LUT, the contrast is increased. That is, when this is controlled by making the inclination G value of the straight line showing the gradation conversion characteristic, the intercept S value the gradation conversion parameter, the density range of The output image, contrast can be adjusted.

The G value is determined by the following equation (4) for finding the inclination of the gradation characteristic curve CV in the screen/film system shown in FIG. 8.

$$G=(J2-J1)/(\log E2-\log E1) \quad (4)$$

Herein, J1=0.25+Fog. J2=2.0+Fog. Fog=0.2

E1, E2 are incident X-ray amount corresponding to respectively J2, J1.

When human each part such as chest part or bust is the observation object, in many case, as G value, generally a value of the degree of about 2.5-5.0 is used.

Further, S value is found by the following equation (5).

$$S=QR \times K1/K2 \quad (5)$$

Herein, QR is The quantization area value, and K1 is the arrived X-ray amount whose signal value is 1535 (QR=200, output density is 1.2), K2 is the image after The gradation conversion, and the actual arrived X-ray amount of the image whose output density is 1.2. The value of K1 is uniquely determined at the setting of the quantization area QR value before photographing.

(Gradation Reversal Processing)

The gradation reversal processing is the processing by which the density corresponding to the gradation level is reversed. For example, when the minimum gradation is 0 (display density: black)-the maximum gradation is 4095 (display density: white), this is reversed and allocated to the display density: white, when the minimum gradation is 0, and display density: black, when the maximum gradation 4095.

(Noise Reduction Processing)

The noise reduction processing is the processing by which the reduction of the noise component included in the image signal of the X-ray image, is intended. Herein, an example in which the degree of the reduction of noise is made large, in the low density part in which noise is easily conspicuous, and the degree of suppression of noise is decreased in the high density part in which noise is hardly conspicuous, will be described.

In the noise reduction processing, each processing of the multiple resolving power decomposition processing, edge. noise information obtaining processing, smoothing processing, edge emphasis. noise suppression processing, restoring processing is successively conducted.

Figure 10:
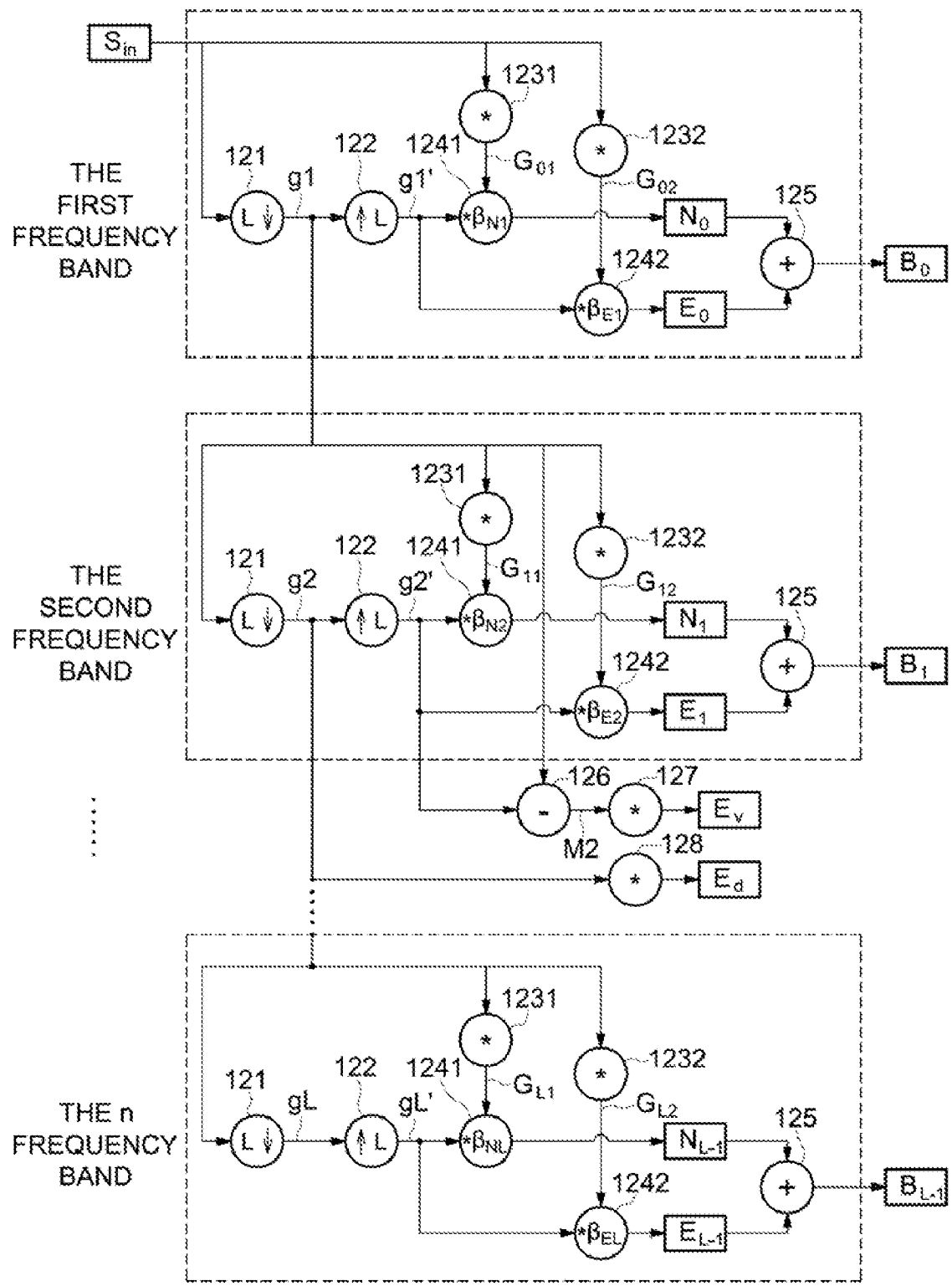
FIG. 10 is a view showing a part of the flow of the noise reduction processing.

Initially, referring to FIG. 10, the multiple resolving power decomposition processing, edge noise information obtaining processing, smoothing processing, edge emphasis. noise suppression processing, will be described. FIG. 10 is a view showing the relationship between each processing and the image signal.

(Multiple Resolving Power Decomposition Processing)

In the multiple resolving power decomposition processing, when the original image signal Sin is multiple resolving power-converted, un-sharp image signal gk' of a plurality of spatial frequency band (k=1–L (L is an integer more than 1, hereinafter, it is same) is obtained.

In the multiple resolving power conversion, a low-pass filter is used. By the low-pass filter, the filter processing 121 is conducted on the original image signal Sin, and when the original image signal Sin after the processing is sampled by 1 pixel (down sampling), the un-sharp image signal g1 is generated. This un-sharp image signal g1 is the largeness of ¼ of the original image.

Next, the pixel of a value of [0] is complemented for each sampling interval of the un-sharp image signal g1 by the interpolation processing 122. This supplement is conducted when the pixel row and the pixel line of a value of [0] are inserted into for each row and line composing the un-sharp image signal g1. Hereupon, because in the un-sharp image signal interpolated in this manner, the pixel in the case of [0] is inserted for each 1 pixel, change of the signal value is under the condition that it is not smooth. Then, after such an interpolation, the filtering is conducted again by the low-pass filter, un-sharp image signal g1' is obtained. In this un-sharp image signal g1', the change of the signal value is under the condition that it is smooth as compared to the un-sharp image signal just after the above-described interpolation.

This un-sharp image signal g1' when after the image is made ¼, the interpolation of 0 and the filtering are conducted for each 1 pixel, becomes the same size as the original image signal, and under the condition that the frequency higher than half of the spatial frequency of the original image signal is removed.

Further, in order to obtain the un-sharp image signal of the frequency band which is 1 step lower, the filter processing 121 is conducted on the un-sharp image signal g1. Hereby, the un-sharp image signal g1 is further converted into the un-sharp image signal g2 whose largeness is ¼ (¹⁄₁₆ of the original one), which is sampled for each 1 pixel. Then, the interpolation processing 122 is conducted on this un-sharp image signal g2, and the un-sharp image signal g2' is generated.

When such processing is successively repeated, the un-sharp image signal gk of each frequency band (resolving power) of the first –n whose frequency characteristic is different, the un-sharp image signal gk' can be obtained.

(Edge Noise Information Obtaining Processing)

The edge noise information obtaining processing is the processing by which, in a plurality of frequency bands obtained by the multiple resolving power de-composition processing, the edge information and noise information in the original image signal Sin are obtained based on the un-sharp image signal of any frequency band. Herein, an example in which they are obtained based on the un-sharp image signal of the second frequency band is described, however, it is preferable that the frequency band as the reference is the frequency band whose pixel size is a degree of 0.5-1.0 (mm) pitch and which is not the maximum frequency band. For examples in the case where an image of the pixel size is 0.175 pitch and the down-sampling ratio is 1/2, the third frequency band is most preferable. This is for the reason that to the pseudo micro edge image in which the Gaussian noise is added to the edge signal of a degree of 30 step/1-2 mm, the noise. contrast ratio is the highest, and it becomes the condition that the edge is easily recognized.

Initially, the obtaining method of the edge information will be described. In the edge information, the edge component information Ev and edge direction information Ed are included. In advance, the obtaining method of the edge component information Ev will be described. As shown in FIG. 10, initially, the differential image signal M2 of the un-sharp image signal G1 and un-sharp image signal g2' is found by the difference processing 126. From this difference image signal M2, the edge component information Ev is obtained by the comparing processing 127.

In the comparing processing 127, the concerning pixel is set in the differential image signal M2. The signal value of the concerning pixel and threshold value Bh, B1 are compared, when the signal value is more than the threshold value Bh, it is judged that the concerning pixel composes the positive edge component, and when the signal value is less than the threshold value B1, the concerning pixel composes the negative edge component. The threshold values Bh, B1 are threshold values previously prepared for discriminating respectively the positive edge component, negative edge component.

On the one hand, when the signal value is less than the threshold value Bh and more than the threshold value B1, adjoining pixel of the concerning pixel is referred, and it is judged whether the adjoining pixel is positive or negative edge component. When the adjoining pixel has positive or negative edge component, it is judged that the concerning pixel is the edge inflection point. The edge inflection point is a point near the signal value 0 which is the turning point of positive, negative of the edge component, and a point of the reference of the edge. Further, when the adjoining pixel does not have the edge component of positive or negative, it is judged that the concerning pixel is non-edge component.

When the component of the concerning pixel is judged, the judgment result (any of positive edge component, negative edge component, edge inflection point, non-edge component) is made the edge component information Ev, corresponds to the information of the pixel position, and is stored in the memory part 35. The above described processing is conducted by being repeated for all pixels.

Figure 11A:
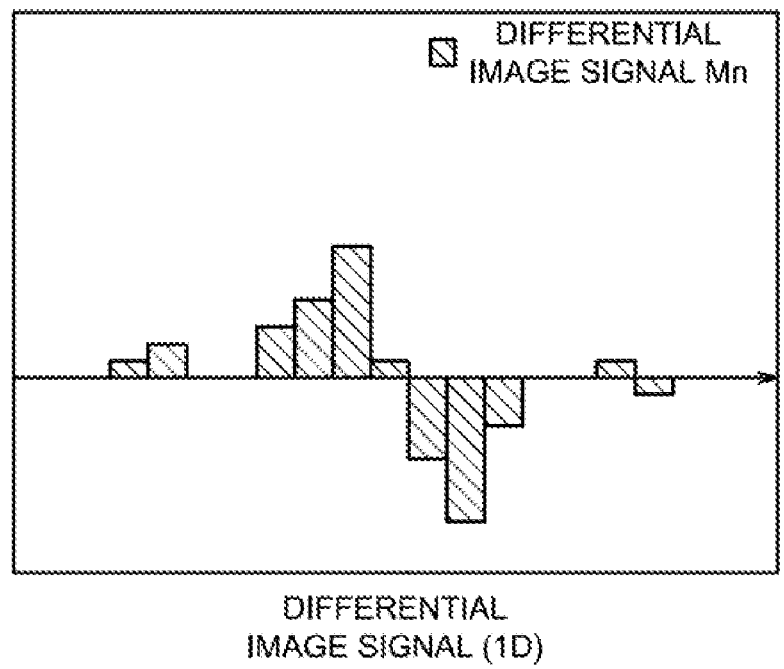
FIG. 11($a$) is a view typically showing the image signal for one row having the differential image signal.
Figure 11B:
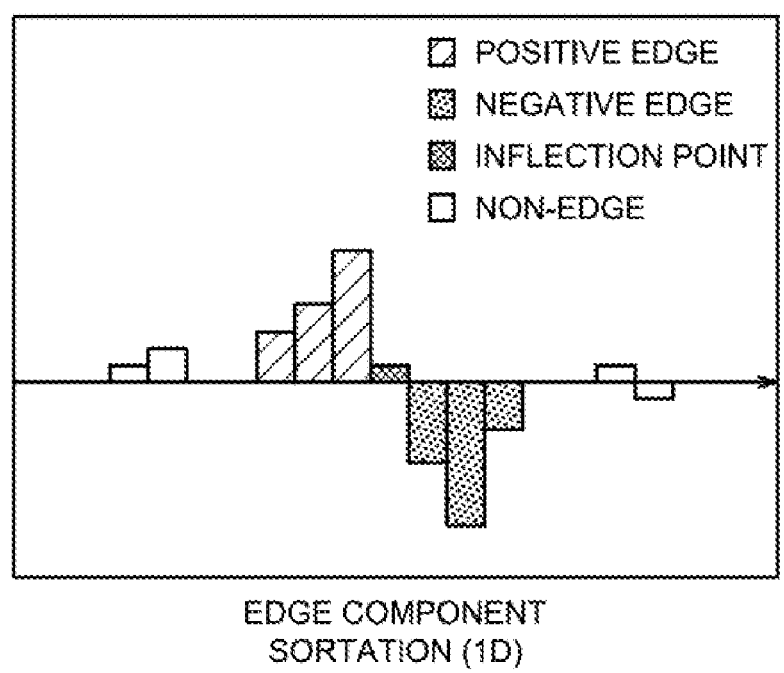

FIG. 11(a) is a view typically showing the image signal for one row in which the differential image signal M2 exists. FIG. 11(b) shows the typical view in which the edge component (positive edge component, negative edge component, edge infliction point, non-edge component) of the differential image signal M2 is classified, based on the edge component information Ev obtained for the differential image signal M2 in FIG. 11(a).

Next, the obtaining method of the edge direction information Ed will be described. The edge direction information Ed is obtained when un-sharp image signal g2' is filter processed 128 by the Sobel filter, Prewitt filter.

In the above edge information obtaining process, pixels whose edge component represents non-edge component do not form an edge. Next, the obtaining method of the noise information Ns for these pixels (non-edge pixels) will be described.

When the differential image signal between the un-sharp image signal gn-1', and the un-sharp image signal gn' is Mn (in the case of the first frequency band, the differential signal between the original image signal Sin and the un-sharp image signal g1'), the noise information Ns can be obtained from, for example, the local dispersal value in the differential image signal Mn in each frequency band, entropy value information and its pixel position information.

The entropy value Se of the image cab be found by the following equation (6) (refer to "Digital Image Processing 3rd Edition" published by Wiley-Interscience Co.) by using the provability (z) which some pixel takes pixel value z, and the gradation number Z of the image.

[Arith 3]

$$Se = -\sum_{z=0}^{Z-1} P(Z)\log 2\{P(Z)\} \quad (6)$$

When the entropy value is lower than a predetermined value in the intermediate frequency band (the second -n frequency band) and the entropy is larger than in the maximum frequency band (the first frequency band), the noise component is dominative in the pixel position, and the pixel in its pixel position can be made the noise component. Accordingly, as the noise information Ns, the information showing that the pixel is the noise component is made correspondent to the information of the pixel position, and stored in the memory part 35.

The obtained edge information Ev, Ed, the noise information Ns are used in the smoothing and density dependency correcting processing 1231, 1232. In the processing 1231, 1232, based on the edge information Ev, Ed, and/or the noise information Ns, the smoothing processing, density dependent correction processing are conducted on the original image signal Sin, and the un-sharp image signal gk (k=1-(L-1)) of each frequency band. The smoothing processing is conducted by being separated into the edge smoothing processing, and the noise smoothing processing. That is, the smoothing and density dependency correcting processing 1231 conducts the density dependent correction processing after the edge smoothing processing, and the smoothing and density dependency correcting processing 1232 conducts the density dependant correction processing after the noise smoothing processing. The processed signal G01 is outputted from the smoothing and density dependency correcting processing 1231, and the processed signal G02 is outputted from the smoothing and density dependency correcting processing 1232.

(Smoothing Processing)

As the filter used for the smoothing, the low-pass filter used for the multiple resolving power decomposition processing, or the frequency respond low-pass filter close to it is preferable. In FIGS. 12(a), 12(b), its filter example is shown. The filter example shown in FIG. 12(a) is an example of 2 dimensional smoothing filter used when the down sampling of the multiple resolving power decomposition is conducted by Laplacian pyramid method by which binomial filtering is conducted 8-times. For this smoothing filter, the smoothing filter coefficient (5 taps) is 2 dimensionally set. When the tap number is 5 taps, the filter coefficient F(x) is expressed by the function shown by the following equations (7), (8).
[Arith 4]

$$f_{1D}[i] = 0.303 \cdot \exp\left(-\frac{i^2}{4}\right) \quad (7)$$

$$f_{2D}[i, j] == 0.092 \cdot \exp\left(-\frac{i^2 + j^2}{4}\right) \quad (8)$$

On the one hand, the filter example shown in FIG. 12(b) is an example of 1-dimensional smoothing filter used when the down sampling of the multiple resolving power decomposition is conducted by the Laplacian pyramid method by which binomial filtering is conducted 8-times.

Initially, the edge smoothing processing will be described. In the edge smoothing processing, the edge component information Ev of each pixel is obtained from the memory part 35, and based on this edge component information Ev, the pixel of edge component is judged for each of the original image signal Sin and the un-sharp image signal gk (k=1–(L–1))pf each frequency band. Then, 1-dimensional smoothing processing is conducted only in the edge inclination direction by the smoothing filter (refer to for example, FIG. 12(b)) aiming at the pixel of edge component on the original image signal Sin and the un-sharp image signal gk of each frequency band. Hereby, the image signal mainly composed of noise component and the frequency component of the 1-step lower frequency band is obtained. That is, the edge smoothing processing is the processing by which the image signal in which the signal intensity of the edge component is decreased and the noise component is emphasized is obtained.

Next, the noise smoothing processing will be described.

In the noise smoothing processing based on the edge component information Ev of each pixel obtained from the memory part 35, the pixel of the non-edge component, edge component, is discriminated respectively for the original image signal Sin, and the un-sharp image signal gk (k=1–(L–1)) of each frequency band. Then, for each image of the original image signal Sin, and the un-sharp image signal gk, by the smoothing filter (refer to, for example, FIG. 12(a)), 2nd dimensional smoothing processing is conducted aiming at the pixel of non-edge component. Further, for the pixel of the edge component, by the smoothing filter (refer to, for example, FIG. 12(b)), 1-dimensional smoothing processing is conducted only in the direction except of the edge inclination direction, or only in the direction perpendicular to the edge inclination direction. Hereby, only the image signal mainly composed of the edge component, and the frequency component of 1-step lower frequency band, is obtained.

(Density Dependent Correction Processing)

The density dependent correction processing is the processing by which, in order to suppress the arch-fact, the generation of noise generated in the noise suppression processing 1241, edge emphasis processing 1242 in the latter stage, the correction is previously conducted for the image signal after smoothing processing. In the correction, the degree of its correction is controlled by the density of the image signal (image signal value). Specifically, it is the processing by which the correction component value is obtained by the correction function R shown in FIG. 13, and this correction component value is subtracted from the image signal value obtained after the smoothing processing.

The correction function R is a function by which the correction component value is obtained from the image signal value and contrast. The contrast is a signal value of the differential image signal (for the original image signal Sin, the differential image signal to the un-sharp image signal g1 of the maximum frequency band) between mutual un-sharp image signal gk of the adjoining frequency band before the density dependent correction processing. Hereupon, the correction functions R are respectively prepared corresponding to for the processing signal of the edge smoothing processing, for the processing signal of the noise smoothing processing, and the edge smoothing processing, noise smoothing processing, and respectively defined for each frequency band.

Such a correction is conducted is for the reason that, in the noise suppression processing 1241, edge emphasis processing 1242, when the degree of processing is made large, there is a case where the image quality is reversely damaged by the generation of arch-fact or the amplification of the noise. In the edge emphasis processing 1242, the partial degradation of the image quality by the generation of the arch-fact becomes a problem, in the noise suppression processing 1241, the amplification of the noise component becomes a problem. Such an arch-fact or noise is particularly easily conspicuous in the low density part. Accordingly, it is necessary that in the low density part, the density dependant correction processing is conducted so that the degree of the processing of the edge emphasis, noise suppression is small.

Figures 12, 13:
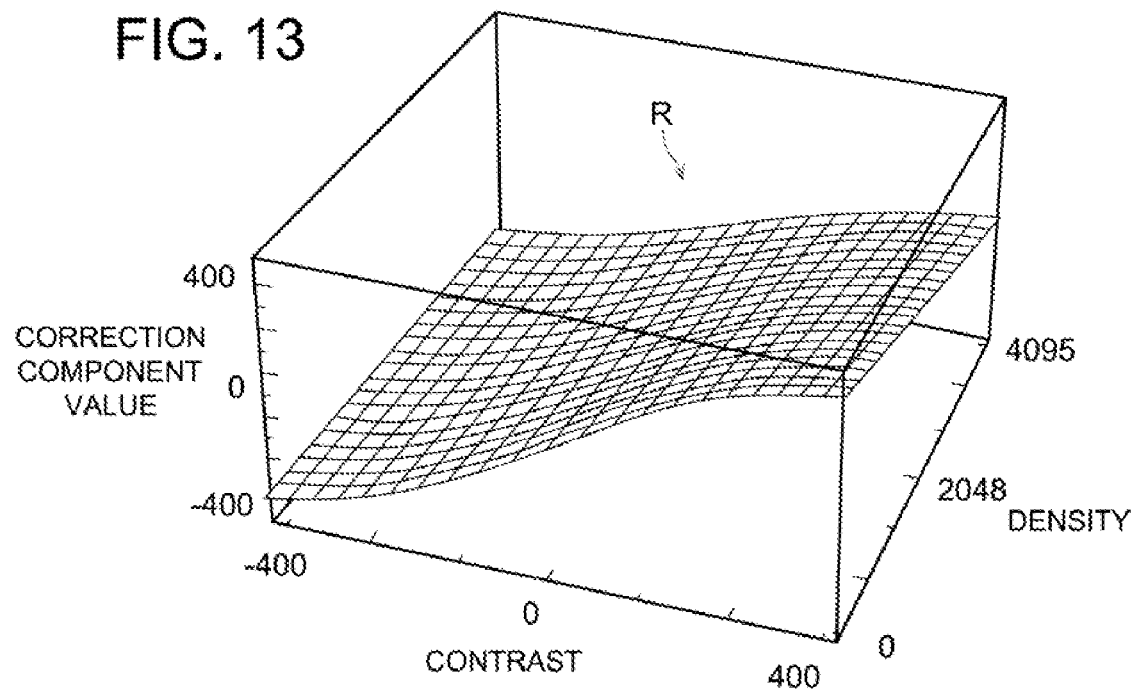
FIG. 12($a$) is a view showing an example of 2-dimensional smoothing filter coefficients.
FIG. 13 is a view showing an example of the correction functions used in the density dependent correction processing.
Figure 14:
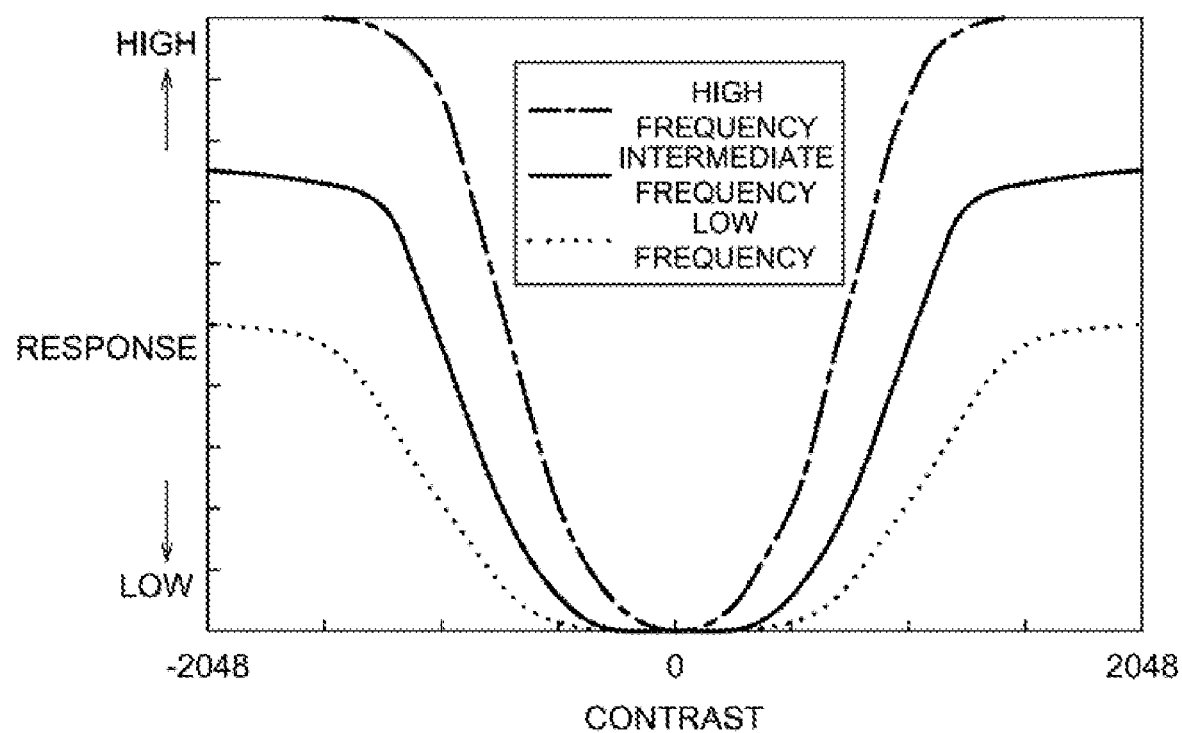
FIG. 14 is a view showing the response to the contrast of the correction function of FIG. 13.

The differential image signal is an image signal when it is a signal in which the edge smoothing processing is conducted, which is composed mainly of noise component, and when it is a signal in which the noise smoothing processing is conducted, which is composed mainly of the image component. As shown in FIG. 13, when the correction function R is designed in such a manner in the low density and as the value of the differential image signal is near 0, the correction component value becomes large, it can be controlled so that, in the low density part, the signal component which is added to the original image signal Sin is small, that is, the degree of the edge emphasis noise suppression is small.

Figure 15:
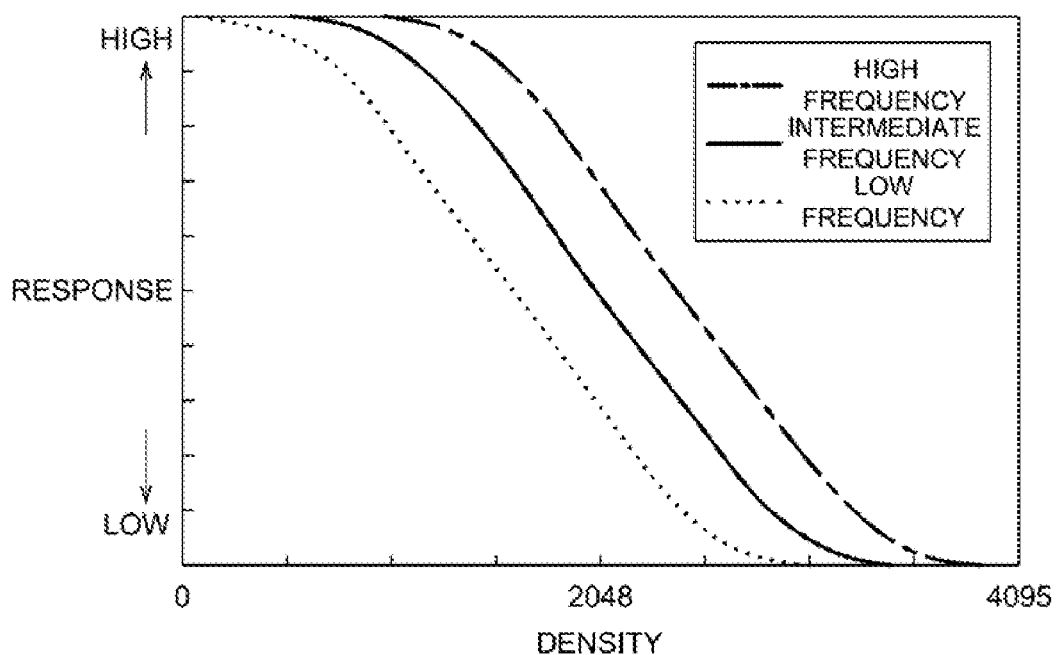
FIG. 15($a$) is a view showing the response to the density of the correction function corresponding to the noise smoothing processing.
Figure 15:
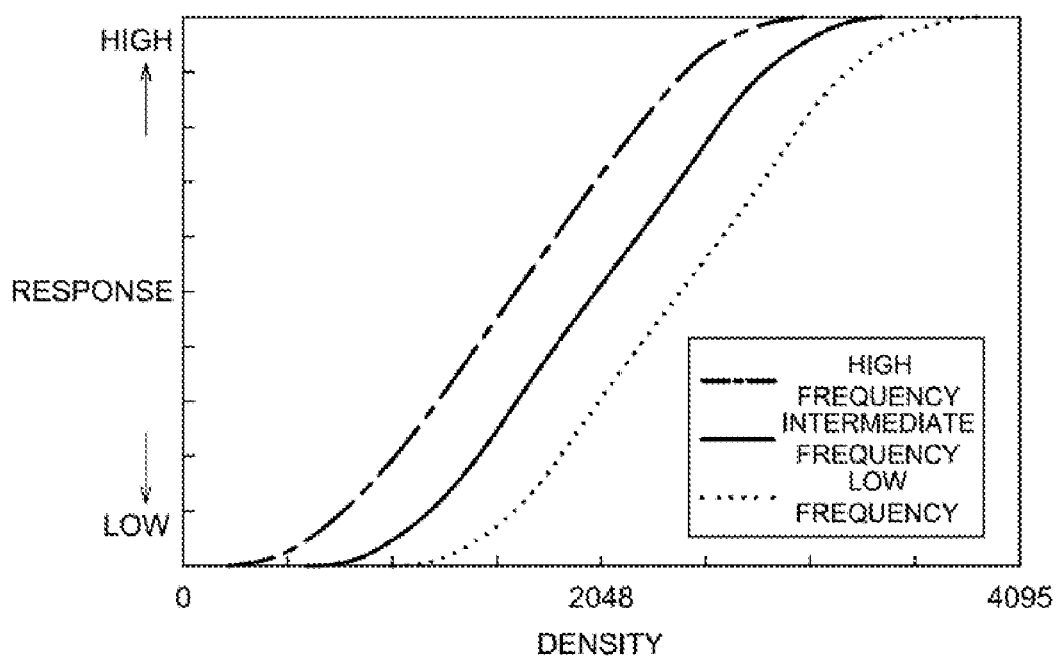

On the one hand, FIG. 15 is a view expressing the response (gain) to the density of the correction function R. FIG. 15(a) is a view showing the response to the density of the correction function R corresponding to the noise smoothing processing. As shown in FIG. 15(a), the degree of correction becomes large in the low density part than the high density part, and it can be seen that the degree of the edge emphasis processing to the high density part becomes large.

On the one hand, FIG. 15(b) is a view showing the response to the density of the correction function R corresponding to the edge smoothing processing. As shown in FIG. 15(b), the degree of the correction is large in the high density part then the low density part, and it can be seen that, in the low density part, the degree of the noise suppression processing becomes large.

In this manner, when, by the density dependant correction processing, it is controlled so that, in the low density part in which the noise is easily conspicuous, the degree of the noise suppression processing is made large, and the degree of the edge emphasis processing is made small, the noise can be reduced. On the one hand, when it is controlled so that, in the high density part in which the noise is hardly conspicuous, the degree of the noise suppression processing is made small, the degree of the edge emphasis processing is made large, the generation of the noise, arch-fact can be reduced.

(Edge Emphasis•Noise Suppression Processing)

In the noise suppression processing 1241, the subtraction of the processed signal G01 obtained from the processing 1231, and the un-sharp image signal g1' IS conducted. The subtraction is conducted between pixels to which each image signal corresponds. Then, the noise suppression coefficient βN1 is multiplied on the differential image signal which is mainly composed of the noise component, and obtained by the subtraction, and the differential image signal N0 in which the noise component is decreased, is obtained. The noise suppression coefficient is prepared for each frequency band, and expressed by βNk ($-1<\beta Nk<0$)

In the same manner, in the emphasis processing 1242, the subtraction is conducted between the processed signal G02 obtained by the processing 1232 and the un-sharp image signal g1'. Then, the edge emphasis coefficient βE1 is multiplied on the differential image signal mainly composed of the edge component obtained by the subtraction, the differential image signal E0 in which the edge component is emphasized, is obtained. The edge emphasis coefficient is prepared for each frequency band, is expressed by βEk ($0<\beta Ek<1$).

Then, by the addition processing 125, the differential image signal N0, E0 are added, the differential image signal B0 is obtained. When the above described processing is conducted in each frequency band, the differential image signal Bk−1 (k=1−L) is obtained. The obtained differential image signal Bk−1 is stored in the memory part 35.

Figure 16:
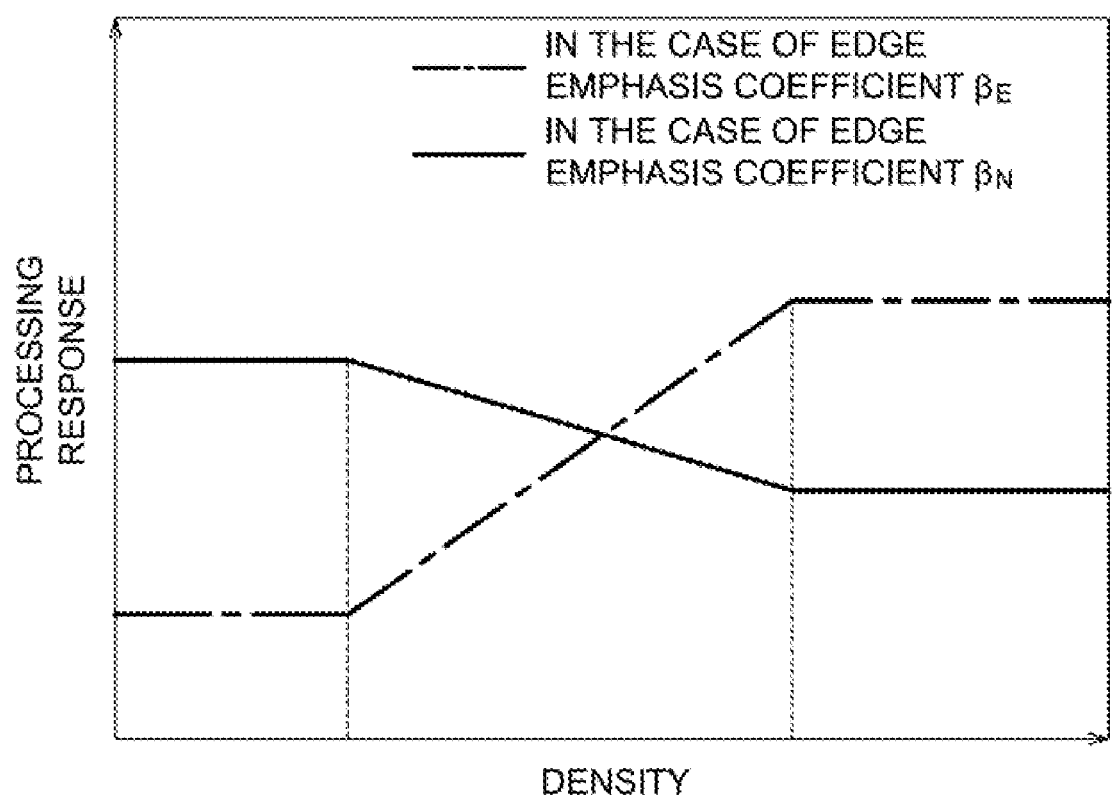
FIG. 16 is a view showing the processing response to the density of the edge emphasis processing, and the processing response to the density of the noise suppression processing.

FIG. 16 is a view showing the relationship (characteristic shown by the solid line) between the processing response and the density when, in the noise suppression processing 1241, the noise suppression coefficient βNk is multiplied, and the relationship (characteristic shown by the dotted line) between, in the edge emphasis processing 1242, the processing response and the density when, in the edge emphasis processing 1242, the edge emphasis coefficient βEk is multiplied. As shown in FIG. 16, as the result that the density dependent correction processing is conducted individually on the signal of the noise component (signal after the edge smoothing processing), the signal of the edge component (signal after the noise smoothing processing), in the low density part, the degree of the noise suppression processing becomes large, the degree of the edge emphasis processing is decreased. Hereby, in the low density part, it is possible that the noise is hardly conspicuous. Further, in the high density part in which the noise is hardly conspicuous, the degree of the noise suppression processing becomes small, and the degree of the edge emphasis processing becomes large. Hereby, in the high density part, the degree of the noise suppression processing is made small, while the arch fact which is generated by the noise suppression processing, is decreased, it is possible that the edge is more emphasized.

(Restoring Processing)

Figure 17:
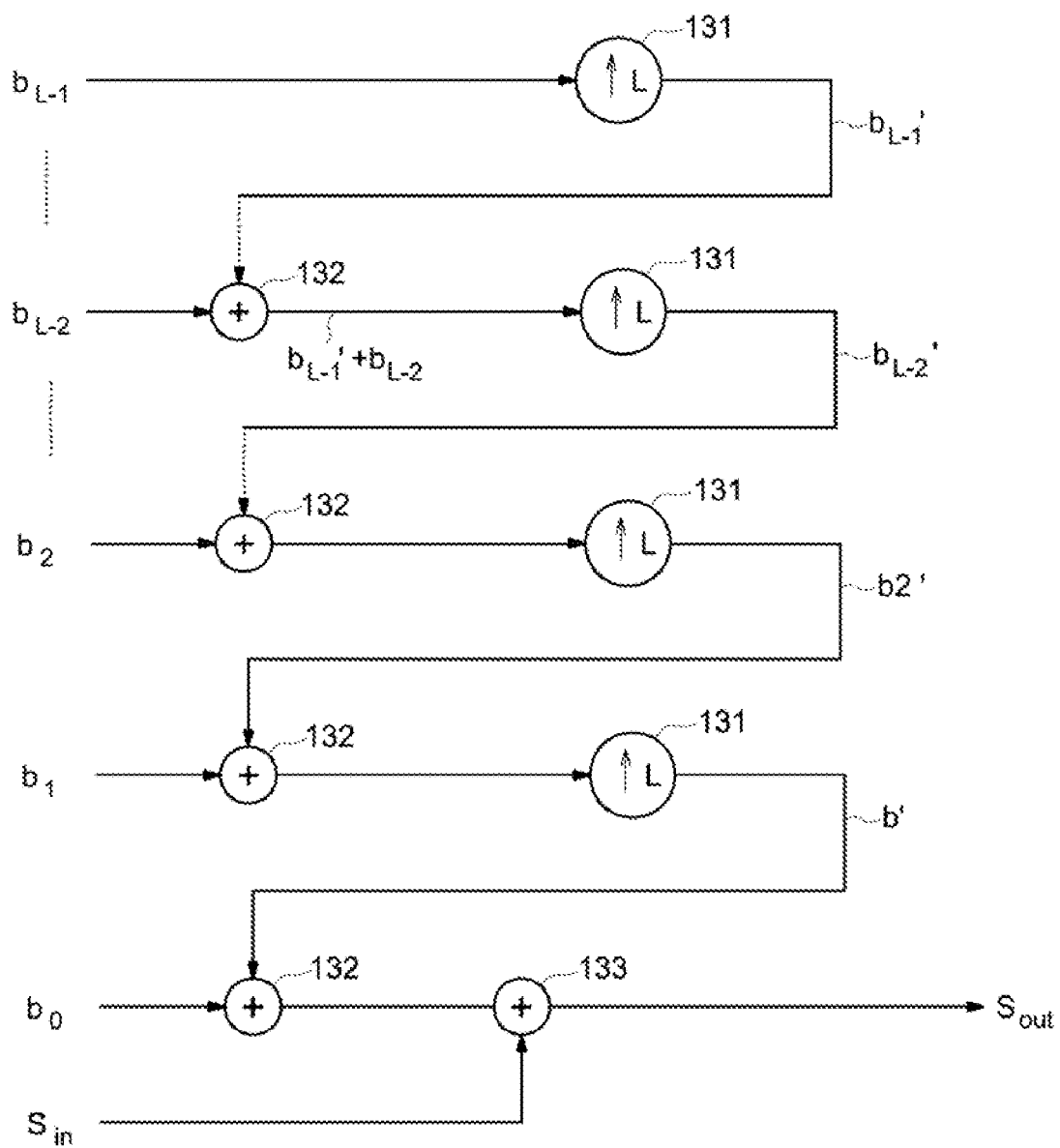
FIG. 17 is a view showing a part of the flow of the noise reduction processing.

The restoring processing is a processing by which, as shown in FIG. 17, the differential image signal bk−1 is added to the original image signal Sin and reversely-converted. Hereupon, in the present embodiment, by Laplacian pyramid method, the reverse conversion (restoring) is conducted from a plurality of detailed images. By this Laplacian pyramid method, the rapid processing becomes possible, however, the other method can also be used.

Initially, the interpolation processing is conducted on the differential image signal bL−1 of the lowest frequency band, interpolated between each pixel, and the image signal bL−1' which is formed of 4 digits, is formed. Next, mutual corresponding pixels of the interpolated image signal bL−1' and the un-sharp image signal bL−2 whose frequency band is 1 step higher, are added, and the addition image signal (bL−1'+bL−2) is obtained.

Next, the interpolation processing is conducted on this addition image signal (bL−1'+bL−2), between each pixel is interpolated and further, the image bL−2' whose largeness is 4 times is obtained. Next, the mutual pixels corresponding to the interpolated image bL−2' and the un-sharp image signal bL−3 whose frequency band is 1 step higher, are added, and the addition image signal (bL−2'+bL−3) is obtained.

The above-described processing is repeated to the differential image signal bk whose frequency is higher. Then, finally, when the signal in which the image signal b1' and the differential image signal b0 having the maximum resolving power are added, is added to the original image signal Sin, the processed image signal Sout is obtained.

The image processing condition for the child is as follows. When the gradation conversion processing for the child is conducted, G value is made larger than G value for general photographing, in the noise reduction processing, the noise suppression coefficient βNk of the noise suppression processing is set to a larger value than the value for the general photographing, the degree of the noise suppression is made large. Alternatively, G value is made smaller than G value for the general photographing, in the noise suppression processing, the edge emphasis coefficient βEk for the edge emphasis processing is set to the larger value than the general photographing, and the degree of the edge emphasis is made large.

Generally, in many cases, G vale in the gradation conversion processing of the hip joint image for the child is given by the degree of 2.0-2.2. Further, the coefficients βNk, βEk according to the noise suppression, edge emphasis are different by the X-ray amount of the image itself, object of the diagnosis, however, βNk is about 0.2-0.6, βEk is about 0-0.4. For example, when, on the X-ray image of the edge component SE=100, the noise component SN=100, the image processing is conducted under the image processing condition of G value 2.0, βNk=0.4, βEk=0.2, the edge component SE, noise component SN in the concerning area after the image processing are respectively SE=240, SN=120, and the ratio SE/SN is SE/SN=240/120=2.0.

In order to maintain SN constant and to increase SE, for example, it may be made that G value is 3.0, βNk=0.6, βEk=0.2. That is, G value is increased and βNk is increased.

On the one hand, in order to maintain SE constant, and to increase SN, for example, it may be made that G value is 1.5, βNk=0.4, βEk=0.6. That is, G value is decreased and βEk is increased.

When the child is the photographic subject, the phase contrast photographing is conducted. In the case of X-ray image obtained by the phase contrast photographing, the side edge of the human organization is originally the edge emphasized image. Accordingly, in the noise reduction processing, the edge component and the noise component can be accurately extracted, and in the noise reduction processing, when it is through the above edge emphasis processing 1242, the edge of the side edge part is more emphasized. Further, because it is the photographing in short time, by using the X-ray of low energy, the signal value is low and the noise is easily generated as compared to the general photographing. However, in the noise reduction processing, when it is through the noise suppression processing, the noise in the low signal value (low density part) can be reduced as much as possible, and by the synergistic action with the above edge emphasis, the sharper image quality can be obtained.

Figure 18:
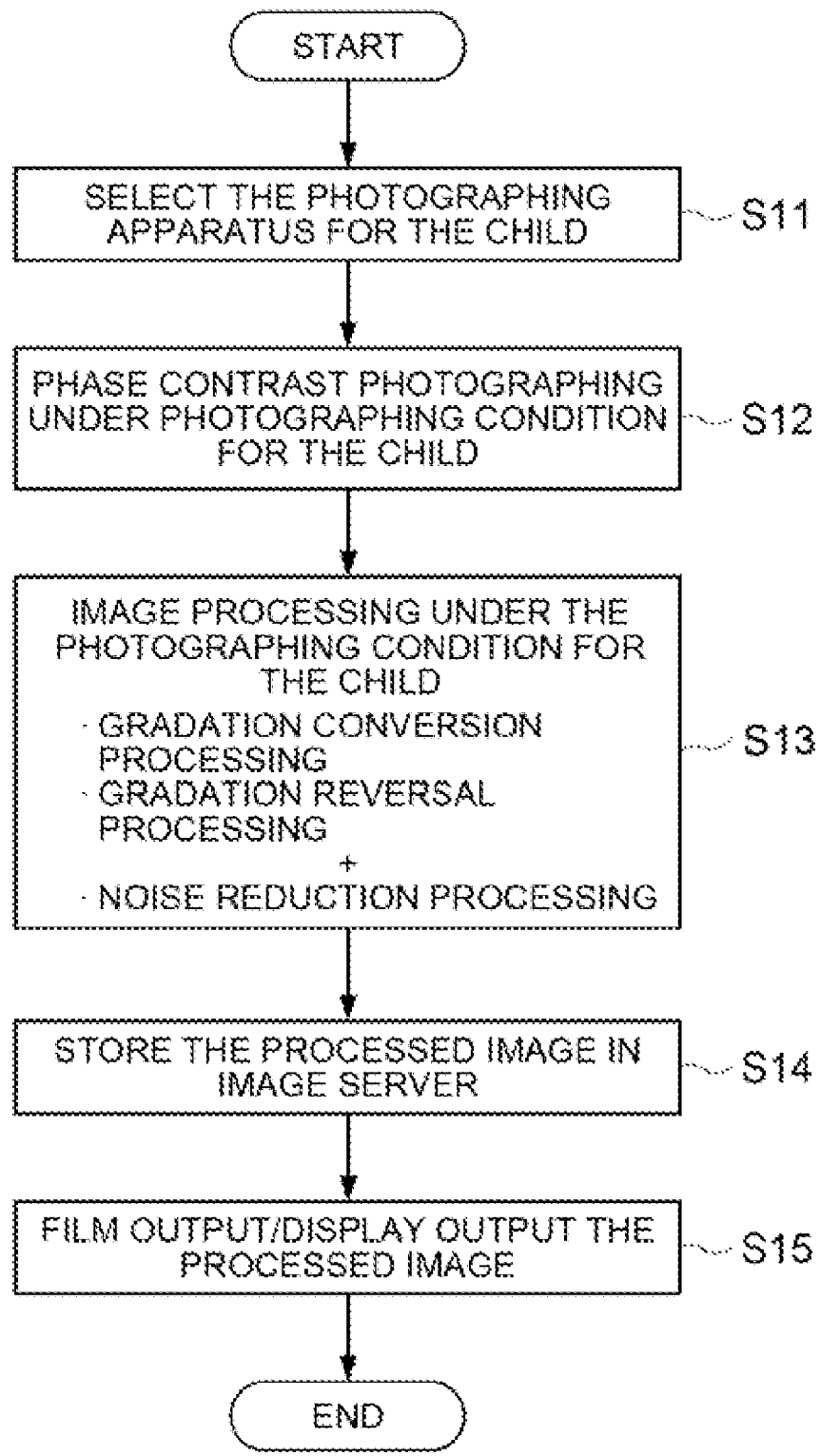
FIG. 18 is a view explaining the flow of the total motions in the X-ray image processing system.

Next, the operation of the X-ray image processing system will be described. FIG. 18 is a flowchart showing the flow from the photographing to the output of the X-ray image in the X-ray image processing system 1. When the photographing in which the child is the subject, is conducted, the control server 20 transmits the photographing order information to the photographing apparatus 10b by which the photographing can be conducted under the photographing condition for the child (Step S11). In the photographing apparatus 10b, following the photographing order information, the phase contrast photographing is conducted by the photographing condition for the child (Step S12). That is, the focal size D of the X-ray irradiated from the X-ray source 2 is 30-200 (μm), the tube voltage is made less than 50 kVp, the magnifying power M is $1.2 \leq M \leq 5$, $R1 \geq (D-7)/200$, the distance R2 is made within the range of $R2 \geq 0.15$. Further, the photographing time is within 0.02 s.

The image detector 6 for the photographed image is loaded into the reading apparatus 10d by the photographer. The reading apparatus 10d conducts the reading processing, the data of X-ray image is generated. Then, the image processing condition is written in the header of the generated X-ray image, and is made the incidental information relating to the image generation. After that, following the control of the control server 20, the data of the X-ray image is transmitted from the reading apparatus 10d to the image processing apparatus 30. Hereupon, in the control server 20, the identification of the X-ray image is conducted as follows. Initially, the identification number previously attached to the image detector 6 used for the photographing is inputted by the photographer, the control server 20 makes the identification number correspond to the photographing order information and stores. Then, in the reading apparatus 10d, when the X-ray image is read from the image detector 6, the identification number of the image detector 6 is also read, and the information of this identification number is attached to the X-ray image. In the control server 20, when the identification number attached to the X-ray image is referred to, the photographing order information of the X-ray image is discriminated based on the identification number, the x-ray image can be identified.

In the image processing apparatus 30, following the control of the control server 20, the image processing is conducted on the data of the X-ray image by the image processing condition for the child. The image processing is conducted in the order of the noise reduction processing after the gradation conversion processing, or the gradation reverse processing after the noise reduction processing (Step S13). In the gradation conversion processing, G value is increased and in the noise reduction processing, the degree of the noise suppression is made large. Or G value is reduced, in the noise reduction processing, the noise suppression is conducted, and the edge emphasis whose degree of the emphasis is large, is conducted.

When each image processing is completed, the image processing apparatus 30 writes the image processing condition in the header of the X-ray image data, and makes it the attached information relating to the image processing. After that, by the control of the control server 20, the data of the X-ray image is transmitted to the image server 40. In the image server 40, the storing processing of the X-ray image data is conducted (Step S14).

The control server 20 receives the transmission request from the image diagnostic apparatus 50b, 50c, for the X-ray image data stored in the image server 40, and the control signal indicating that the transmission requested X-ray image data is transferred to the image diagnostic apparatus 50a, 50b, is transmitted to the image server 40. In the image server 40, according to this control information, the specified X-ray image data is transmitted to the reading apparatus 50a, 50b.

In the image diagnostic apparatus 50b, 50c, the display and output of the x-ray image data are conducted. When the indication operation of the output to the film is conducted by the doctor, the X-ray image data is transmitted to the film output apparatus 50a. In the film output apparatus 50a, the film output of the received X-ray image data is conducted (Step S15).

Examples

In the X-ray image processing system, the photographing (Comparative examples 1, 2, Examples 1-3) is conducted under the following experimental condition, and the visual reviewing for the output image in which the obtained X-ray image is outputted to the film, is conducted.
(Experimental Condition)
The subject: the hip-joint part of the simulated phantom (made by Kyoto Kagaku Co.) in which the child is simulated is photographed.

The photographing apparatus: as the photographing apparatus, the apparatus which is produced in the trial production by Konica Minolta Co. is used.

The X-ray source: in comparative examples 1, 2, conventionally used Medical use W anode X-ray tube (A192 by Varian Co.) is used. The foal point diameter is 1200 (μm). On the one hand, in Examples 1-3, the W anode X-ray tube made in trial production by Konica Minolta Co. is used. The focal size D is 100 (μm).

The image detector: As the fluorescent plate, Kegius plate made by the same Co. is used.

The reading apparatus: Kegius model 190 made by the same Co. is used. The reading pitch is 87.5 μm.

The output apparatus: DRYPR0 model 793 made by the same Co.
(Photographing Condition)
X-ray energy: X-ray energy was adjusted as shown in Table 1 by controlling tube voltage.

Tube current: 100 mA

The photographing time: varied in the range of 0.005-0.02 (s).

The photographing distance: in Comparative examples 1, the magnifying power M=1, the photographing distance R1 is 0.5, R2 is 0 m. In Examples 1-5 and Comparative example 2, the magnifying power M=2, the photographing distances R1, R2 are respectively 0.5 m.
(Image Processing Condition):

Comparative examples 1, 2 and Examples 1-3: the image processing (noise reduction processing) was not applied, Examples 4, 5: the gradation conversion processing of G value 1.5, the noise reduction processing of βNk=0.4, βEk=0.6 are conducted.
(Review Reference)

The image quality of the hip-joint part of the X-ray image which is output-formed on the film is reviewed. In the image quality review, the sharpness and the granularity are reviewed in a comprehensive way.

A: It can be very clearly visually recognized.
B: It can be clearly visually recognized.
C: It can be visually recognized.
D: It can not be visually recognized.

According to the above-described review reference, 7 image reviewers observe the image on the film and the image review is conducted.
(Result of Evaluation)

In Table 1, the result of the review is shown.

TABLE 1

| | X-ray tube | Focal point diameter (μm) | Magnifying power M | Distance (m) | | X-ray energy (keV) | Tube current (mA) | Photo-graphing time (s) | mAs value | Noise elimination | Review |
|---|---|---|---|---|---|---|---|---|---|---|---|
| | | | | R1 | R2 | | | | | | |
| Comparative Example 1 | *1 | 1200 | 1 | 0.5 | 0 | 28 | 100 | 0.01 | 1 | No | D |
| Example 1 | *2 | 100 | 2 | 0.5 | 0.5 | 28 | 100 | 0.02 | 2 | No | A |
| Example 2 | *2 | 100 | 2 | 0.5 | 0.5 | 28 | 100 | 0.01 | 1 | No | B |
| Example 3 | *2 | 100 | 2 | 0.5 | 0.5 | 28 | 100 | 0.005 | 0.5 | No | C |
| Example 4 | *2 | 100 | 2 | 0.5 | 0.5 | 28 | 100 | 0.005 | 0.5 | Yes | B |
| Example 5 | *2 | 100 | 2 | 0.5 | 0.5 | 20 | 100 | 0.005 | 0.5 | Yes | A |
| Comparative Example 2 | *2 | 100 | 2 | 0.5 | 0.5 | 33 | 100 | 0.01 | 1 | No | D |

*1: Conventionally used medical use W anode X-ray tube
*2: Trial production W anode X-ray tube Hereupon, in Table 1, the mAs value is a value obtained when the tube current value is multiplied by the photographing time. The mAs value is proportional to an amount of radiation, that is, the greater the mAs is, the more the amount of radiation is increased.

In Table 1, it can be seen that the X-ray image according to Examples 1-5, was the good image quality in the sharpness, granularity.

In comparison of Comparative example 2 and Example 2, although the amount of radiation was equal to each other, good image was obtained in Example 2. This was owing to the effect of the phase contrast radiography according to the present invention.

In comparison of Example 1 and Example 3, the photographing time in Example 3 was shorter than Example 1, that is, the amount of radiation in Example 3 was reduced to 25% of that Example 1. However, an image having no practical problem was obtained. Accordingly, according to the present invention, even if the amount of radiation is reduced, it is clear that an image quality equivalent to the conventional good image before reducing the amount of radiation can be obtained.

In comparison of Example 3 and Example 4, although the amount of radiation was equal to each other, the image quality in Example 4 was improved. This was owing to the effect of the noise reducing processing conducted in Example 4. Therefore, even if the amount of radiation is reduced, the image quality can be improved by the application of the noise reducing processing according to the present invention.

In comparison of Example 2 and Comparative example 2, although the amount of radiation was equal to each other, the image quality in Comparative example 2 was deteriorated. This is owing to the reason that the X-ray energy in Comparative example 2 was made higher that the upper limitation (30 keV) of the range of the present invention. Therefore, in order to obtain the effect of the phase contrast radiography, it is necessary to adjust the X-ray energy not to exceed 30 keV.

Incidentally, if the X-ray energy was adjusted to be lower than the lower limitation (15 keV) of the range of the present invention, since an amount of exposure absorbed in an object is increased, such a low X-ray energy is not preferable.

In Examples 3 and 4, the photographing time is 0.05 s which is short time, and enough image quality is obtained. During the photographing, it is difficult that the child is made motion-less. Accordingly, even when it is a short time photographing, when the X-ray image of good visibility can be obtained, it is very preferable structure from the viewpoint of the easiness of photographing operation, exposed amount to the child. Further, because the blur following the child motion generated between the photographing, can be suppressed, the sharpness of the image quality is good direction as compared to the conventional method whose photographing time is long. Further, in Examples 1-5, compared to Comparative Examples 1, 2, totally good image quality is obtained. It is considered as one of factors that, when the focal size is made 100 μm which is the small focal size, the spread of the blur B in the phase contrast effect is suppressed, the edge emphasis effect is increased. Hereupon, in Examples 1-5, also when the magnifying power M is varied in the range of 1.2-5, the review result which is the same as the above description is obtained.

As described above, according to the present embodiment, when the child is the photographing subject, the X-ray image is obtained by the phase contrast photographing, and the noise reduction processing is conducted on this. Because in the X-ray image obtained by the phase contrast photographing, the side edge of the subject organization is edge emphasized, in the noise reduction processing, the noise component is separated and the edge component is easily extracted, the edge emphasis and the noise suppression can be accurately conducted. That is, because the sharp and high quality processing image can be obtained, in the photographing for the child, even when the X-ray amount at the photographing is a small amount of radiation, the X-ray image with the image quality enough for the photographing, can be obtained. Further, in the case where the image quality is prior, when the photographing is conducted without particularly adjusting the X-ray amount, the X-ray image with sharper and higher image quality than at the time of ordinary photographing can be obtained.

Further, in the noise reduction processing, by the edge emphasis coefficient $\beta Ek$ and the noise reduction coefficient $\beta Nk$, the degree of the edge emphasis and the noise reduction can be separately adjusted. Therefore, the processing whose degree of freedom is high can be conducted. Further, when the density dependent correction processing is conducted, the generation of noise or arch fact following the noise suppression can be suppressed.

Further, when the gradation conversion processing, gradation reverse processing are conducted in addition to the noise reduction processing, the image quality of the X-ray image can be effectively increased. For example, when G value, in the gradation conversion processing, the coefficient $\beta Ek$ and the coefficient $\beta Nk$ in the noise reduction processing are adjusted, the noise component and the edge component can be adjusted. Further, because the low X-ray amount is used for the photographing for the child, the signal value of whole X-ray image becomes small, although the noise and the image signal can hardly be distinguished, when after the noise reduction processing, the gradation reverse processing is conducted, the visibility of the noise can be further lowered.

Hereupon, the above embodiment is an example to which the present invention is applied, it is not limited to this. For example, because the X-ray amount is decreased at the time of photographing for the child, the sensitivity of the image detector may also be increased. When the fluorescent body plate is used for the image detector, the photo-multiplier sensitivity is increased. When FPD is used, it is considered that the gain of the amplifier is increased.

Further, as the fluorescent body plate of the image detector, the granularity type whose granularity is emphasized and the sharpness type whose sharpness is emphasized, may also be selected. The granularity type is a type in which the thickness of the fluorescent body plate is adjusted to large. When the fluorescent body layer is made thick, because the X-ray energy amount which can be accumulated, becomes large, the signal value becomes high as a whole, the X-ray image with low noise can be obtained. On the one hand, the sharpness type is a type whose thickness of the fluorescent body plate is adjusted to small. When the fluorescent body layer is made thin, the reflection of the incident X-ray in the fluorescent body layer is reduced and the blur by the reflection is reduced, the X-ray image whose sharpness is high can be obtained.

What is claimed is:

1. An X-ray image processing system, comprising:
   a radiographing section including an X-ray source to emit X-rays for an object to be radiographed and an image detector to detect X-rays having passed through the object, wherein the radiographing section is adapted to conduct a phase contrast radiography by providing a space between the object and the image detector and by irradiating X-rays having an X-ray energy of 15 to 30 (keV) from the X-ray source to the object;
   an image data producing section to produce X-ray image data of X-ray image detected by the image detector;
   an image processing section to apply an image processing including a noise reducing process and an edge enhancement process for the produced X-ray image data; and
   an output section to output the processed image data applied with the image processing,
   wherein the image data producing section comprises:
      a density-related correcting section to control the noise reducing process and the edge enhancement process in accordance with an image density level of pixels of the X-ray image data such that a degree of noise reduction for pixels having a low image density level is higher than a degree of noise reduction for pixels having a high image density level and a degree of edge enhancement for pixels having a high image density level is higher than a degree of edge enhancement for pixels having a low image density level.

2. The X-ray image processing system described in claim 1, wherein when D represents a focal size of the X-ray source, R1 represents a distance between the X-ray source and the object and R2 represents a distance between the object and the X-ray detector, the X-ray source, the object and the X-ray detector are arranged to satisfy the following formulas:

$(D-7)/200 \leq R1 \leq 1.0$ (m), and $0.15 \leq R2 \leq 1.0$ (m).

3. The X-ray image processing system described in claim 2, wherein R1 satisfies the following formula:

$0.3 \leq R1 \leq 1.0$ (m).

4. The X-ray image processing system described in claim 2, wherein R2 satisfies the following formula:

$0.3 \leq R2 \leq 1.0$ (m).

5. The X-ray image processing system described in claim 2, wherein the X-ray source has a focal size D of 30 to 200 µm.

6. The X-ray image processing system described in claim 5, wherein the X-ray source has a focal size D of 50 to 120 µm.

7. The X-ray image processing system described in claim 2, wherein when M represents an enlargement ratio represented by Formula of ((R1+R2)/R1) in the phase contrast radiography, M satisfies the following formula:

$1.2 \leq M \leq 5$.

8. The X-ray image processing system described in claim 7, wherein M satisfies the following formula:

$1.5 \leq M \leq 3$.

9. The X-ray image processing system described in claim 1, wherein the image processing includes a gradation converting process, and after the image processing section applies the gradation converting process for the X-ray image data in the image processing, the image processing section applies the noise reducing process for the X-ray image data so as to form the processed image data.

10. The X-ray image processing system described in claim 1, wherein the image processing includes a gradation reversing process, and after the image processing section applies the noise reducing process for the X-ray image data in the image processing, the image processing section applies the gradation reversing process for the X-ray image data so as to form the processed image data.

11. The X-ray image processing system described in claim 1, wherein the image processing section comprises:
   a decomposition processing section to conduct a multiple-resolution conversion for X-ray image data inputted from the image data producing section so as to obtain unsharp image data for each of plural different frequency bands;
   a conversion processing section to conduct a converting process for at least one of the inputted X-ray image data and the unsharp image data of the plural different frequency bands so as to obtain converted image data and to obtain difference image data by subtracting between the converted image data and image data in a frequency band neighboring the converted image data or image data in the highest frequency band; and
   a reconstruction processing section to add the difference image data to the inputted X-ray image data so as to obtain the processed image data.

12. The X-ray image processing system described in claim 11, wherein the conversion processing section comprises:
   an information acquiring subsection to acquire at least one of edge information and noise information in the inputted X-ray image data;
   a smoothing correcting section to conduct at least one of an edge smoothing process and a noise smoothing process for at least one of the inputted X-ray image data and the unsharp image data of the plural frequency bands based on at least one of the edge information and the noise information and thereafter conduct the density-related correcting process by the density-related correcting section for the smoothed image data so as to obtain the converted image data.

13. The X-ray image processing system described in claim 12, wherein the smoothing correcting section comprises:
   an edge component adjusting subsection including:
      a first converting section to obtain first converted image data by conducting the noise smoothing process for at least one of the inputted X-ray image data and the unsharp image data of the plural frequency bands based on at least one of the edge information and the noise information and thereafter to conduct the density-related correcting process for the noise-smoothed image data so as to obtain the first converted image data, and a first difference adjusting section to obtain difference image data mainly composed of edge components by subtracting the first converted image data and image data in a frequency band neighboring the first converted image data or image data in the highest frequency band and to multiply the difference image data with a predetermined edge adjustment coefficient so as to obtain edge component-adjusted difference image data; and a noise component adjusting section including:

a second converting section to obtain second converted image data by conducting the edge smoothing process for at least one of the inputted X-ray image data and the unsharp image data of the plural frequency bands based on at least one of the edge information and the noise information and thereafter to conduct the density-related correcting process for the edge-smoothed image data so as to obtain the second converted image data, and a second difference adjusting section to obtain difference image data mainly composed of noise components by subtracting the second converted image data and image data in a frequency band neighboring the second converted image data or image data in the highest frequency band and to multiply the difference image data with a predetermined noise adjustment coefficient so as to obtain noise component-adjusted difference image data.

14. The X-ray image processing system described in claim 12, wherein the edge information includes information representing at least one of pixel positions of edge components, signs of image data, directions of edge components, and pixel positions of inflection points, and the noise information includes information represent at least one of local dispersion values, entropy values and pixel positions of noise components.

15. The X-ray image processing system described in claim 12, wherein the noise smoothing process conducts smoothing two dimensionally for pixels being not edge components and conducts smoothing one dimensionally for pixels being edge components in a direction other than an edge inclination direction or a direction perpendicular to an edge inclination direction.

16. The X-ray image processing system described in claim 12, wherein the edge smoothing process conducts smoothing one dimensionally for pixels being edge components only in an edge inclination direction.

17. An X-ray image processing method of processing an X-ray image of a child of six years old or under, comprising the steps of:

arranging the child and a detector to provide a space therebetween;

irradiating X-rays having an X-ray energy of 15 to 30 (keV) from the X-ray source to the child with a phase contrast radiography;

producing X-ray image data of the child by detecting X-rays having passed through the child;

applying a noise reducing process and an edge enhancement process for the X-ray image data on an image processing condition to enhance an X-ray image taken out from the children, and applying a density-related correcting section to control the noise reducing process and the edge enhancement process in accordance with an image density level of pixels of the X-ray image data such that a degree of noise reduction for pixels having a low image density level is higher than a degree of noise reduction for pixels having a high image density level and a degree of edge enhancement for pixels having a high image density level is higher than a degree of edge enhancement for pixels having a low image density level.

18. The X-ray image processing method described in claim 17, wherein when D represents a focal size of the X-ray source, R1 represents a distance between the X-ray source and the child and R2 represents a distance between the child and the X-ray detector, the X-ray source, the child and the X-ray detector are arranged to satisfy the following formulas:

$$(D-7)/200 \leq R1 \leq 1.0 \text{ (m)}, \text{ and } 0.15 \leq R2 \leq 1.0 \text{ (m)}.$$

19. The X-ray image processing method described in claim 18, wherein R1 satisfies the following formula:

$$0.3 \leq R1 \leq 1.0 \text{ (m)}.$$

20. The X-ray image processing method described in claim 18, wherein R2 satisfies the following formula:

$$0.3 \leq R2 \leq 1.0 \text{ (m)}.$$

21. The X-ray image processing method described in claim 18, wherein the X-ray source has a focal size D of 30 to 200 µm.

22. The X-ray image processing method described in claim 21, wherein the X-ray source has a focal size D of 50 to 120 µm.

23. The X-ray image processing method described in claim 18, wherein when M represents an enlargement ratio represented by Formula of ((R1+R2)/R1) in the phase contrast radiography, M satisfies the following formula:

$$1.2 \leq M \leq 5.$$

24. The X-ray image processing method described in claim 23, wherein M satisfies the following formula:

$$1.5 \leq M \leq 3.$$

* * * * *